United States Patent
Itagaki et al.

(10) Patent No.: US 9,642,785 B2
(45) Date of Patent: May 9, 2017

(54) SILICON-OXIDE-COATED ZINC OXIDE AND METHOD FOR MANUFACTURING SAME, SILICON-OXIDE-COATED-ZINC-OXIDE-CONTAINING COMPOSITION, AND COSMETIC

(71) Applicant: Sumitomo Osaka Cement Co., Ltd., Tokyo (JP)

(72) Inventors: Tetsuro Itagaki, Tokyo (JP); Yoshiki Kusahara, Tokyo (JP); Gaku Fujihashi, Tokyo (JP); Syunsuke Suma, Tokyo (JP)

(73) Assignee: SUMITOMO OSAKA CEMENT CO., LTD. (JP)

( * ) Notice: Subject to any disclaimer, the term of this patent is extended or adjusted under 35 U.S.C. 154(b) by 58 days.

(21) Appl. No.: 14/783,135

(22) PCT Filed: Mar. 31, 2014

(86) PCT No.: PCT/JP2014/059503
§ 371 (c)(1),
(2) Date: Oct. 8, 2015

(87) PCT Pub. No.: WO2014/171322
PCT Pub. Date: Oct. 23, 2014

(65) Prior Publication Data
US 2016/0045411 A1 Feb. 18, 2016

(30) Foreign Application Priority Data

Apr. 19, 2013 (JP) .................................. 2013-088752
Apr. 19, 2013 (JP) .................................. 2013-088864
May 27, 2013 (JP) .................................. 2013-111009
May 27, 2013 (JP) .................................. 2013-111010
Oct. 31, 2013 (JP) .................................. 2013-227470

(51) Int. Cl.
*A61K 8/27* (2006.01)
*A61K 8/25* (2006.01)
*B01J 2/00* (2006.01)
*A61K 8/02* (2006.01)
*C09C 1/04* (2006.01)
*A61Q 17/04* (2006.01)
*A61K 8/11* (2006.01)

(52) U.S. Cl.
CPC ............. *A61K 8/27* (2013.01); *A61K 8/0241* (2013.01); *A61K 8/11* (2013.01); *A61K 8/25* (2013.01); *A61Q 17/04* (2013.01); *B01J 2/006* (2013.01); *C09C 1/043* (2013.01); *A61K 2800/413* (2013.01); *A61K 2800/621* (2013.01); *A61K 2800/651* (2013.01); *C01P 2002/86* (2013.01); *C01P 2004/04* (2013.01); *C01P 2004/64* (2013.01); *C01P 2004/84* (2013.01)

(58) Field of Classification Search
None
See application file for complete search history.

(56) References Cited

U.S. PATENT DOCUMENTS

2010/0003202 A1* 1/2010 Matsumoto ............ A61K 8/027
424/59

FOREIGN PATENT DOCUMENTS

| JP | H0859238 A | 3/1996 |
|---|---|---|
| JP | 2851885 B2 | 1/1999 |
| JP | 3187440 B2 | 7/2001 |
| JP | 2002308716 A | 10/2002 |
| JP | 2004059421 A | 2/2004 |
| JP | 2007525396 A | 9/2007 |
| JP | 2008266283 A | 11/2008 |
| JP | 2008280465 A | 11/2008 |
| JP | 4582439 B2 | 11/2010 |
| WO | WO9817730 A1 | 4/1998 |

OTHER PUBLICATIONS

Casu et al. Journal of Non-Crystalline Solids 2003 315:97-106.*
Yabuki et al. Physical Chemistry Chemical Physics 2002 4:4830-4837.*
International Search Report of PCT/JP2014/059503 dated Jun. 24, 2014.
F. Grasset et al., "Surface modification of zinc oxide nanoparticles by aminopropyltriethoxysilane", Journal of Alloys and Compounds, Oct. 6, 2003, vol. 360, No. 1-2, pp. 298-311.

* cited by examiner

*Primary Examiner* — Robert A Wax
*Assistant Examiner* — Caralynne Helm
(74) *Attorney, Agent, or Firm* — Merchant & Gould P.C.

(57) ABSTRACT

Provided are a silicon-oxide-coated zinc oxide capable of suppressing the elution of zinc ions from zinc oxide particles, a method for manufacturing the same, a silicon-oxide-coated-zinc-oxide-containing composition, and a cosmetic. The silicon-oxide-coated zinc oxide is a silicon-oxide-coated zinc oxide formed by coating the surfaces of zinc oxide particles with a silicon oxide coating, in which the average particle diameter of the zinc oxide particles is in a range of 1 nm or more and 50 nm or less, when the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$, and furthermore, the decomposition ratio of Brilliant Blue generated by the photocatalytic activity of the zinc oxide particles is 3% or less.

13 Claims, 3 Drawing Sheets

SILICON-OXIDE-COATED ZINC OXIDE AND METHOD FOR MANUFACTURING SAME, SILICON-OXIDE-COATED-ZINC-OXIDE-CONTAINING COMPOSITION, AND COSMETIC

TECHNICAL FIELD

The present invention relates to a silicon-oxide-coated zinc oxide and a method for manufacturing the same, a silicon-oxide-coated-zinc-oxide-containing composition, and a cosmetic and, more specifically, to a silicon-oxide-coated zinc oxide preferably used, particularly, for a facial lotion, a sunscreen gel, an emulsion, a cream, a foundation, a lipstick, rouge, eyeshadow, and the like which require an ultraviolet ray-screening function, a method for manufacturing the same, a silicon-oxide-coated-zinc-oxide-containing composition, and a cosmetic.

The present application is a U.S. National Stage Application of PCT/JP2014/059503, filed on Mar. 31, 2014, which claims priority to Japanese Patent Application No. 2013-88864, filed on Apr. 19, 2013, Japanese Patent Application No. 2013-88752, filed on Apr. 19, 2013, Japanese Patent Application No. 2013-111010, filed on May 27, 2013, Japanese Patent Application No. 2013-111009, filed on May 27, 2013, and Japanese Patent Application No. 2013-227470, filed on Oct. 31, 2013, the contents of all of which are hereby incorporated by reference in their entireties.

BACKGROUND ART

Ultraviolet radiation has become a cause of the deterioration of a number of materials such as a resin and rubber and is said to, for human beings, possibly act as a cause of not only sun tanning or sunburn but also an aging phenomenon or skin cancer. Therefore, an ultraviolet ray-screening agent is widely used in the fields of films, paints, cosmetics, and the like.

As the ultraviolet ray-screening agent, organic ultraviolet ray-screening agents such as a benzophenone-based ultraviolet ray-screening agent, a methoxycinnamic acid-based ultraviolet ray-screening agent, and a dibenzoylmethane-based ultraviolet ray-screening agent or inorganic ultraviolet ray-screening agents such as zinc oxide and titanium oxide are generally used.

The organic ultraviolet ray-screening agents have problems in that there is a concern that the organic ultraviolet ray-screening agents may deteriorate due to heat or the prolonged exposure to ultraviolet radiation, and a single kind of organic ultraviolet ray-screening agent is not capable of absorbing ultraviolet rays in a wide range and thus it is necessary to use a combination of multiple kinds of organic ultraviolet ray-screening agent having different ultraviolet ray absorption wavelengths.

On the other hand, the inorganic ultraviolet ray-screening agents have an effect of absorbing ultraviolet rays having wavelengths that correspond to the band gaps of inorganic particles included in the inorganic ultraviolet ray-screening agent and advantages that the inorganic ultraviolet ray-screening agents do not deteriorate due to heat or the prolonged exposure to ultraviolet radiation, have excellent weather resistance, heat resistance, and the like, and are capable of screening ultraviolet rays in a wide wavelength range since the inorganic ultraviolet ray-screening agents screen ultraviolet rays through scattering attributed to the refractive index of the inorganic particles.

By the way, since the inorganic ultraviolet ray-screening agents scatter not only ultraviolet rays but also visible light rays, even the inorganic ultraviolet ray-screening agents having the above-described advantages have a problem in that the skin easily becomes whitish when a large amount of the inorganic ultraviolet ray-screening agent is blended into a cosmetic or the like. Therefore, in order to cope with the above-described problem, an appropriate combination of the inorganic ultraviolet ray-screening agent and the organic ultraviolet ray-screening agent is used.

As the inorganic ultraviolet ray-screening agent, titanium oxide, zinc oxide, and the like are generally used. Particularly, zinc oxide is capable of screening ultraviolet rays in a wide wavelength range from the UV-A region (320 nm to 400 nm) to the UV-B region (280 nm to 320 nm).

For example, when zinc oxide and titanium oxide are compared with each other in terms of the photocatalytic activity through which a substance in contact with the surfaces of particles is oxidized, zinc oxide has extremely lower photocatalytic activity. In addition, the refractive index of zinc oxide is 2.0, which is lower than the refractive index of titanium oxide (2.7), and thus, in a case in which zinc oxide is made into nanoparticles, the zinc oxide particles have excellent transparency. As a result, zinc oxide has been attracting attention as an ultraviolet ray-screening agent.

Meanwhile, since zinc is an amphoteric element, zinc oxide, which is an oxide of zinc, has characteristics of easily dissolving in an acid and an alkali, in addition, slightly dissolving in water as well, and releasing zinc ions, and these characteristics prevent zinc from becoming a sufficiently stable element.

In addition, while zinc oxide has an extremely lower photocatalytic activity compared with titanium oxide, the photocatalytic activity is desirably suppressed. For example, in a case in which zinc oxide is made into nanoparticles so that the average particle diameter thereof reaches 50 nm or smaller, the specific surface area is increased and thus the photocatalytic activity becomes high.

As described above, zinc oxide particles have particularly significant problems of the release of zinc ions and a high photocatalytic activity.

In addition, compared with oil-based cosmetic products, water-based cosmetic products are not sticky and are capable of obtaining a fresh feeling, and thus, in recent years, the water-based cosmetic products have been used as a variety of cosmetics such as sunscreens, emulsions, and creams. In a case in which zinc oxide is used for the water-based cosmetic, zinc ions being eluted react with a water-soluble macromolecule of an organic ultraviolet ray-screening agent or a viscosity improver, and there is a concern that problems of the degradation of performance as a cosmetic, discoloration, a change in the viscosity, and the like may be caused. Therefore, there has been a problem in that the degree of freedom in formulation is limited.

For example, when a carbomer (carboxy vinyl polymer), which is generally used as a viscosity improver, and zinc oxide are jointly used, a zinc ion being eluted and a carboxylate group (COO—) of the carbomer react with each other, and thus the gel structure of the carbomer breaks, and there is a problem in that the viscosity decreases.

As described above, in order to solve the problems of zinc oxide, there have been a variety of proposals regarding zinc oxide coated with an inorganic oxide.

For example, there has been a proposal regarding a method in which zinc oxide is added to an aqueous solution of silicate of soda so as to be brought into a suspended state, and then the hydrogen-ion exponent (pH) is held at approximately 7, thereby obtaining silica-coated zinc oxide (Patent Literature No. 1).

In addition, there has been a proposal regarding a method in which zinc oxide, which is a raw material, is brought into contact with a composition for forming a silica coating containing silicic acid or a precursor capable of generating silicic acid, which does not contain an organic group and a halogen, water, an alkali, and an organic solvent, thereby obtaining silica-coated zinc oxide which does not deteriorate by weather due to the photocatalytic activity (Patent Literature No. 2).

In addition, there has been a proposal regarding a method in which zinc oxide powder is coated with at least one of organopolysiloxanes and silicone compounds (excluding silane compounds) in a non-gaseous state, and is fired at a temperature in a range of 600° C. to 950° C. in an oxidizing atmosphere, thereby obtaining activity-suppressing zinc oxide powder coated with silicon oxide (Patent Literature No. 3).

CITATION LIST

Patent Literature

[Patent Literature No. 1] Japanese Patent No. 2851885
[Patent Literature No. 2] Japanese Patent No. 4582439
[Patent Literature No. 3] Japanese Patent No. 3187440

SUMMARY OF INVENTION

Technical Problem

However, in the methods described in Patent Literature 1 and 2, there have been no studies regarding the elution of zinc ions, and thus, even when a coating treatment is carried out on zinc oxide using silica, there has been a problem in that it is difficult to sufficiently suppress the elution of zinc ions from zinc oxide.

In addition, in the method described in Patent Literature 3, after the surfaces of zinc oxide powder are coated with an organopolysiloxane and a silicone compound, it is necessary to fire the organopolysiloxane and the silicone compound at a high temperature of 600° C. or higher in order to oxidize the organopolysiloxane and the silicone compound so as to form a coating of silicon oxide on the surfaces of the zinc oxide powder. However, the firing at a high temperature accelerates the crystal growth of zinc oxide, and thus there has been a problem in that it is difficult to use this method for silica-coated zinc oxide having a small primary particle diameter, for example, 50 nm or smaller.

The present invention has been made in consideration of the above-described circumstances, and an object of the present invention is to provide a silicon-oxide-coated zinc oxide capable of suppressing the elution of zinc ions from zinc oxide particles, a method for manufacturing the same, a silicon-oxide-coated-zinc-oxide-containing composition, and a cosmetic.

Solution to Problem

As a result of repeating intensive studies in order to solve the above-described problems, the present inventors found that, when the surfaces of zinc oxide particles are coated with a dense silicon oxide coating, complex particles having a so-called core shell structure are produced, and the silicon oxide coating is capable of inhibiting the elution of zinc ions from the zinc oxide particles, and found that, when the silicon-oxide-coated zinc oxide is applied to a cosmetic, the ultraviolet ray-screening function improves, the transparency is also excellent, and furthermore, the problems attributed to the elution of zinc ions are also solved, and thus the present inventors completed the present invention.

That is, a silicon-oxide-coated zinc oxide of the present invention is a silicon-oxide-coated zinc oxide formed by coating the surfaces of zinc oxide particles with a silicon oxide coating, in which the average particle diameter of the zinc oxide particles is in a range of 1 nm or more and 50 nm or less, and, when the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$.

The content ratio of the zinc oxide particles is preferably in a range of 50% by mass or more and 90% by mass or less.

When the silicon-oxide-coated zinc oxide is immersed in an aqueous solution having a hydrogen-ion exponent of 5 so that the content thereof reaches 0.05% by mass, the elution ratio of zinc being eluted in the aqueous solution is preferably 60% by mass or less.

A method for manufacturing the silicon-oxide-coated zinc oxide of the present invention is characterized in that, zinc oxide particles are suspended in a solvent so as to produce a zinc oxide suspension, next, any one or more of alkoxysilanes and oligomers of an alkoxysilane which are decamers or lower oligomers, a catalyst, and water are added to and reacted with the zinc oxide suspension, and then the obtained reaction product is thermally treated at a temperature in a range of 200° C. or more and 550° C. or less.

A silicon-oxide-coated-zinc-oxide-containing composition of the present invention includes the silicon-oxide-coated zinc oxide of the present invention and a solvent.

The silicon-oxide-coated-zinc-oxide-containing composition of the present invention preferably further includes a viscosity improver.

A cosmetic of the present invention is formed by including either or both the silicon-oxide-coated zinc oxide of the present invention and the silicon-oxide-coated-zinc-oxide-containing composition of the present invention in a base.

In addition, the silicon-oxide-coated zinc oxide of the present invention is a silicon-oxide-coated zinc oxide formed by coating the surfaces of zinc oxide particles with a silicon oxide coating, in which the average particle diameter of the zinc oxide particles is in a range of 1 nm or more and 50 nm or less, when the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$, and the decomposition ratio of Brilliant Blue generated by the photocatalytic activity of the zinc oxide particles is 3% or less.

The content ratio of the zinc oxide particles is preferably in a range of 50% by mass or more and 90% by mass or less.

When the silicon-oxide-coated zinc oxide is immersed in an aqueous solution having a hydrogen-ion exponent of 5 so that the content thereof reaches 0.05% by mass, the elution ratio of zinc being eluted in the aqueous solution is preferably 20% by mass or less.

The surfaces of the silicon-oxide-coated zinc oxide are preferably surface-treated with a silicone resin.

The method for manufacturing the silicon-oxide-coated zinc oxide of the present invention is characterized in that, a surface-modified zinc oxide is suspended in a solvent so as to produce a surface-modified zinc oxide suspension, next, any one or more of alkoxysilanes and oligomers of an alkoxysilane which are decamers or lower oligomers, a catalyst, and water are added to and reacted with the surface-modified zinc oxide suspension, and then the obtained reaction product is thermally treated at a temperature in a range of 200° C. or more and lower than 600° C.

The silicon-oxide-coated-zinc-oxide-containing composition of the present invention includes the silicon-oxide-coated zinc oxide of the present invention and a solvent.

The silicon-oxide-coated-zinc-oxide-containing composition of the present invention preferably further includes a viscosity improver.

A cosmetic of the present invention is formed by including either or both the silicon-oxide-coated zinc oxide of the present invention and the silicon-oxide-coated-zinc-oxide-containing composition of the present invention in a base.

Advantageous Effects of Invention

According to the silicon-oxide-coated zinc oxide of the present invention, since the surfaces of zinc oxide particles are coated with a silicon oxide coating, the average particle diameter of the zinc oxide particles is set in a range of 1 nm or more and 50 nm or less, and furthermore, when the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied, it is possible to suppress the elution of zinc ions from the zinc oxide particles to the outside due to the silicon oxide coating that coats the zinc oxide particles. Therefore, in a case in which the silicon-oxide-coated zinc oxide is applied to a cosmetic, it is possible to suppress the degradation of performance as a cosmetic, discoloration, a change in the viscosity, and the like which are caused by the elution of zinc ions.

In addition, according to the method for manufacturing the silicon-oxide-coated zinc oxide of the present invention, since zinc oxide particles are suspended in a solvent so as to produce a zinc oxide suspension, next, any one or more of alkoxysilanes and oligomers of an alkoxysilane which are decamers or lower oligomers, a catalyst, and water are added to and reacted with the zinc oxide suspension, and then the obtained reaction product is thermally treated at a temperature in a range of 200° C. or more and 550° C. or less, it is possible to produce silicon-oxide-coated zinc oxide capable of suppressing the elution of zinc ions from the zinc oxide particles.

According to the silicon-oxide-coated-zinc-oxide-containing composition of the present invention, since the composition includes the silicon-oxide-coated zinc oxide of the present invention and a solvent, it is possible to suppress the elution of zinc element included in the silicon-oxide-coated zinc oxide in the form of zinc ions to the outside. Therefore, it is possible to suppress the degradation of performance as a composition, discoloration, a change in the viscosity, and the like which are caused by the elution of zinc ions.

According to the cosmetic of the present invention, since the cosmetic includes either or both the silicon-oxide-coated zinc oxide of the present invention and the silicon-oxide-coated-zinc-oxide-containing composition of the present invention in a base, it is possible to suppress the elution of zinc element included in either or both the silicon-oxide-coated zinc oxide and the silicon-oxide-coated-zinc-oxide-containing composition in the form of zinc ions to the outside. Therefore, it is possible to suppress the degradation of performance as a cosmetic, discoloration, a change in the viscosity, and the like which are caused by the elution of zinc ions.

According to the silicon-oxide-coated zinc oxide of the present invention, since the surfaces of zinc oxide particles are coated with a silicon oxide coating, the average particle diameter of the zinc oxide particles is in a range of 1 nm or more and 50 nm or less, furthermore, when the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are set to be satisfied, and the decomposition ratio of Brilliant Blue generated by the photocatalytic activity of the zinc oxide particles is set to 3% or less, the surfaces of the zinc oxide particles are uniformly coated with a dense silicon oxide coating, and thus it is possible to suppress the elution of zinc ions from the zinc oxide particles to the outside. Therefore, in a case in which the silicon-oxide-coated zinc oxide is applied to a cosmetic, it is possible to suppress the degradation of performance as a cosmetic, discoloration, a change in the viscosity, and the like which are caused by the elution of zinc ions.

According to the method for manufacturing the silicon-oxide-coated zinc oxide of the present invention, since a surface-modified zinc oxide is suspended in a solvent so as to produce a surface-modified zinc oxide suspension, next, any one or more of alkoxysilanes and oligomers of an alkoxysilane which are decamers or lower oligomers, a catalyst, and water are added to and reacted with the surface-modified zinc oxide suspension, and then the obtained reaction product is thermally treated at a temperature in a range of 200° C. or more and lower than 600° C., it is possible to uniformly cover the surfaces of the zinc oxide particles with a dense silicon oxide coating. Therefore, it is possible to produce silicon-oxide-coated zinc oxide capable of suppressing the elution of zinc ions from the zinc oxide particles.

According to the silicon-oxide-coated-zinc-oxide-containing composition of the present invention, since the composition includes the silicon-oxide-coated zinc oxide of the present invention and a solvent, it is possible to suppress the elution of zinc element included in the silicon-oxide-coated zinc oxide in the form of zinc ions to the outside. Therefore, it is possible to suppress the degradation of performance as a composition, discoloration, a change in the viscosity, and the like which are caused by the elution of zinc ions.

DESCRIPTION OF EMBODIMENTS

Figure 1:
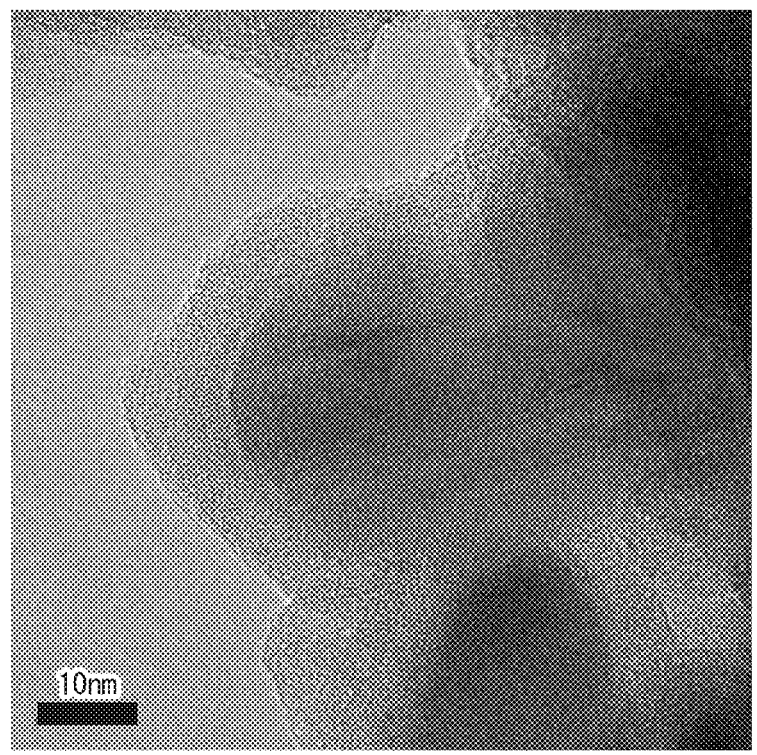
FIG. 1 is a transmission electron microscopic (TEM) image illustrating silicon-oxide-coated zinc oxide of Example 7 of the present invention.

Embodiments for carrying out a silicon-oxide-coated zinc oxide and a method for manufacturing the same, a silicon-oxide-coated-zinc-oxide-containing composition, and a cosmetic of the present invention will be described.

Meanwhile, the following embodiments are the specific descriptions for the better understanding of the gist of the present invention and do not limit the present invention unless particularly otherwise described.

Silicon-Oxide-Coated Zinc Oxide

First Embodiment

A silicon-oxide-coated zinc oxide of an embodiment of the present invention is a silicon-oxide-coated zinc oxide formed by coating the surfaces of zinc oxide particles with a silicon oxide coating, in which the average particle diameter of the zinc oxide particles is in a range of 1 nm or more and 50 nm or less, and, when the abundance ratio of silicon in the silicon oxide coating in a $Q^3$ environment is indicated by $Q^3$, and the abundance ratio in a $Q^4$ environment is indicated by $Q^4$, $Q^3+Q^4>0.6$ and $Q^4/(Q^3+Q^4)≥0.5$.

The content ratio of the zinc oxide particles in the silicon-oxide-coated zinc oxide is preferably in a range of 50% by mass or more and 90% by mass or less. Here, when the content ratio of the zinc oxide particles in the silicon-oxide-coated zinc oxide is lower than 50% by mass, it is not possible to obtain a desired ultraviolet ray-screening effect, and thus it is necessary to use a large amount of silicon-oxide-coated zinc oxide in order to obtain a desired ultraviolet ray-screening effect, which is not preferable. On the other hand, when the content ratio of the zinc oxide particles exceeds 90% by mass, the fraction of the zinc oxide particles in the silicon-oxide-coated zinc oxide becomes too high, and consequently, it becomes impossible to sufficiently cover the surfaces of the zinc oxide particles with a silicon oxide coating, which is not preferable.

The average particle diameter of the silicon-oxide-coated zinc oxide is preferably in a range of 3 nm or more and 500 nm or less, more preferably in a range of 10 nm or more and 300 nm or less, and still more preferably in a range of 20 nm or more and 100 nm or less.

Here, the reasons for limiting the average particle diameter of the silicon-oxide-coated zinc oxide to the above-described range are as described below. When the average particle diameter is smaller than 3 nm, the particle diameters are too small, the surface energy of the obtained silicon-oxide-coated zinc oxide is high, thus, the zinc oxide particles easily agglomerate together, and it becomes difficult to synthesize a silicon-oxide-coated zinc oxide having a desired form and size. On the other hand, when the average particle diameter exceeds 500 nm, the transparency of the silicon-oxide-coated zinc oxide is likely to degrade, and, in a case in which the silicon-oxide-coated zinc oxide is used for a cosmetic or the like, there is a concern that transparency in the visible light range may be impaired.

The "average particle diameter" mentioned herein refers to a numeric value obtained by, when the silicon-oxide-coated zinc oxide is observed using a transmission electron microscope (TEM), a scanning electron microscope (SEM), or the like, selecting a predetermined number of the silicon-oxide-coated zinc oxide particles, for example, 200 or 100 silicon-oxide-coated zinc oxide particles, measuring the longest straight line portions (maximum length diameters) of the respective silicon-oxide-coated zinc oxide particles, and obtaining the weighted average value of the measurement values.

Here, in a case in which the silicon-oxide-coated zinc oxide particles agglomerate together, instead of measuring the agglomerated particle diameters of the agglomerates, the particle diameters of a predetermined number of particles (primary particles) of the silicon-oxide-coated zinc oxide constituting the agglomerate are measured, and the average particle diameter is obtained.

When the silicon-oxide-coated zinc oxide is immersed in an aqueous solution having a hydrogen-ion exponent of 5 for one hour so that the content thereof reaches 0.05% by mass, the elution ratio of zinc being eluted in the aqueous solution is preferably 60% by mass or less, more preferably 20% by mass or less, and still more preferably 10% by mass or less.

The reasons for setting the elution ratio of zinc to 60% by mass or less is that, when the elution ratio of zinc exceeds 60 mass %, the stability of the silicon-oxide-coated zinc oxide degrades, in a case in which the silicon-oxide-coated zinc oxide is applied to a cosmetic, zinc ions being eluted react with a water-soluble macromolecule or the like such as an organic ultraviolet ray-screening agent or a viscosity improver, and the degradation of performance as a cosmetic, discoloration, a change in the viscosity, and the like are caused, which is not preferable.

The elution ratio of zinc can be measured by, for example, dispersing the silicon-oxide-coated zinc oxide in a buffer solution with a pH of 5 so that the content thereof reaches 0.05% by mass, stirring the solution for one hour, then, separating solids and liquids, and measuring the concentration of liquid-phase zinc using an ICP optical emission spectrometry analyzer.

As the buffer solution with a pH of 5, for example, a buffer solution obtained by mixing 500 ml of an aqueous solution of 0.1 M potassium hydrogen phthalate and 226 ml of an aqueous solution of 0.1M sodium hydroxide and then adding water so that the total amount reaches 1000 ml is preferably used as long as the buffer solution is capable of dispersing the silicon-oxide-coated zinc oxide.

Hereinafter, individual constituent elements of the silicon-oxide-coated zinc oxide of the first embodiment will be described in detail.

Zinc Oxide Particles

The average particle diameter of the zinc oxide particles is preferably in a range of 1 nm or more and 50 nm or less, more preferably in a range of 5 nm or more and 50 nm or less, and still more preferably in a range of 10 nm or more and 40 nm or less.

The average particle diameter of the zinc oxide particles can be obtained using the same method as for the above-described silicon-oxide-coated zinc oxide, that is, by, in a casein which the zinc oxide particles are observed using a transmission electron microscope (TEM) or the like, selecting a predetermined number of the zinc oxide particles, for example, 200 or 100 zinc oxide particles from a microscopic view, measuring the longest straight line portions (maximum length diameters) of the respective zinc oxide particles, and obtaining the weighted average value of the measurement values.

When the average particle diameter of the zinc oxide particles is smaller than 1 nm, the crystal structure of the zinc oxide is a space group No. 186, P63mc, a=0.32498 nm, and c=0.52066 nm, and thus sufficient crystallinity cannot be obtained, and the ultraviolet ray-screening performance of the zinc oxide degrades, which is not preferable.

Generally, in a case in which the particle diameters of metallic oxide particles are sufficiently smaller than the wavelengths of light, that is, in a case in which the following expression $$\alpha \pi D / \lambda \quad (1)$$

(here, $\alpha$: particle diameter parameter, D: particle diameter, $\lambda$: the wavelength of light) satisfies $\alpha \ll 1$, generally, in a case in which α<0.4 is satisfied, Rayleigh scattering works, and, in a case in which the particle diameters of the metallic oxide particles are larger than the above case, Mie scattering works.

As described above, in the wavelength range of visible light rays (400 nm to 800 nm), in a case in which the average particle diameter of the zinc oxide particles is 50 nm or smaller, Rayleigh scattering having a relatively low scattering intensity works; however, when the average particle diameter of the zinc oxide particles exceeds 50 nm, the scattering intensities of visible light rays in a wavelength range of 400 nm or higher also increase, and thus, in a cosmetic into which the silicon-oxide-coated zinc oxide of the present embodiment is blended, there is a concern that sufficient transparency may not be obtained with respect to visible light rays.

As the method for synthesizing the zinc oxide particles, there is no particular limitation as long as zinc oxide particles having an average particle diameter in a range of 1 nm or more and 50 nm or less can be synthesized in the method, and examples thereof include dry methods such as a French method (indirect method) and an American method (direct method) and wet methods such as a German method.

Silicon Oxide Coating

The silicon oxide coating is not particularly limited as long as the silicon oxide coating has a high degree of condensation so that "when the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$", which will be described below, are satisfied.

The degree of condensation of silicon oxide can be easily determined by obtaining the NMR spectrum of a silicon-oxide-coated zinc oxide using solid-state $^{29}$Si MAS-nuclear magnetic resonance (NMR) spectroscopy and measuring the area ratios of signals attributed to individual environments of $Q^0$, $Q^1$, $Q^2$, $Q^3$, and $Q^4$ from the peak area ratios of the NMR spectrum.

Here, $Q^n$ (n=0 to 4) indicates a chemical structure determined depending on the number of bridging oxygen atoms, that is, oxygen atoms that bond two Si atoms, out of oxygen atoms in a $SiO_4$ tetrahedral unit which is a constituent unit of silicon oxide.

The area ratios of the signals attributed to these respective environments of $Q^0$, $Q^1$, $Q^2$, $Q^3$, and $Q^4$ are marked as $Q^0$, $Q^1$, $Q^2$, $Q^3$, and $Q^4$. Here, $Q^0+Q^1+Q^2+Q^3+Q^4=1$.

When the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$.

Here, in a case in which $Q^3+Q^4 \geq 0.6$ is satisfied, but $Q^4/(Q^3+Q^4)$ is smaller than 0.5 ($Q^4/(Q^3+Q^4) \leq 0.5$) or in a case in which $Q^4/(Q^3+Q^4) \geq 0.5$ is satisfied, but $Q^3+Q^4$ is smaller than 0.6 ($Q^3+Q^4<0.6$), silicon oxide in the silicon oxide coating does not sufficiently condense, and thus a dense coating cannot be obtained, and consequently, there is a concern that the effect of suppressing the elution of zinc ions in the silicon-oxide-coated zinc oxide may not be sufficiently obtained, which is not preferable.

Second Embodiment

Silicon-Oxide-Coated Zinc Oxide

A silicon-oxide-coated zinc oxide of an embodiment of the present invention is a silicon-oxide-coated zinc oxide formed by coating the surfaces of zinc oxide particles with a dense silicon oxide coating, in which the average particle diameter of the zinc oxide particles is in a range of 1 nm or more and 50 nm or less, when the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$, and the decomposition ratio of Brilliant Blue generated by the photocatalytic activity of the zinc oxide particles is 3% or less.

Meanwhile, there is a close relationship between the "denseness" of the dense silicon oxide coating and the "degree of condensation" of silicon oxide, and the denseness of the silicon oxide coating increases as the degree of condensation of silicon oxide increases.

That is, the "denseness" of the dense silicon oxide coating mentioned herein refers to the state of the silicon oxide coating in which the degree of condensation of silicon oxide is high so that $Q^3+Q^4 \geq 0.6$ and $Q^4/(Q^3+Q^4) \geq 0.5$ are satisfied.

The content ratio of the zinc oxide particles in the silicon-oxide-coated zinc oxide is preferably in a range of 50% by mass or more and 90% by mass or less. Here, when the content ratio of the zinc oxide particles in the silicon-oxide-coated zinc oxide is lower than 50% by mass, it is not possible to obtain a desired ultraviolet ray-screening effect, and thus it is necessary to use a large amount of silicon-oxide-coated zinc oxide in order to obtain a desired ultraviolet ray-screening effect, which is not preferable. On the other hand, when the content ratio of the zinc oxide particles exceeds 90% by mass, the fraction of the zinc oxide particles in the silicon-oxide-coated zinc oxide becomes too high, and consequently, it becomes impossible to sufficiently cover the surfaces of the zinc oxide particles with a silicon oxide coating, which is not preferable.

The average particle diameter of the silicon-oxide-coated zinc oxide is preferably in a range of 5 nm or more and 500 nm or less, more preferably in a range of 10 nm or more and 300 nm or less, and still more preferably in a range of 20 nm or more and 100 nm or less.

Here, the reasons for limiting the average particle diameter of the silicon-oxide-coated zinc oxide to the above-described range are as described below. When the average particle diameter is smaller than 5 nm, the particle diameters are too small, the surface energy of the obtained silicon-oxide-coated zinc oxide is high, thus, the zinc oxide particles easily agglomerate together, and it becomes difficult to synthesize a silicon-oxide-coated zinc oxide having a desired form and size. On the other hand, when the average particle diameter exceeds 500 nm, the transparency of the silicon-oxide-coated zinc oxide is likely to degrade, and, in a case in which the silicon-oxide-coated zinc oxide is used for a cosmetic or the like, there is a concern that transparency in the visible light range may be impaired or friction or the like may be caused and thus the feeling during the use of the cosmetic or the like may deteriorate.

The "average particle diameter" mentioned herein refers to a numeric value obtained by, when the silicon-oxide-coated zinc oxide is observed using a transmission electron microscope (TEM), a scanning electron microscope (SEM), or the like, selecting a predetermined number of the silicon-oxide-coated zinc oxide particles, for example, 200 or 100 silicon-oxide-coated zinc oxide particles, measuring the longest straight line portions (maximum length diameters) of the respective silicon-oxide-coated zinc oxide particles, and obtaining the weighted average value of the measurement values.

Here, in a case in which the silicon-oxide-coated zinc oxide particles agglomerate together, instead of measuring the agglomerated particle diameters of the agglomerates, the particle diameters of a predetermined number of particles (primary particles) of the silicon-oxide-coated zinc oxide constituting the agglomerate are measured, and the average particle diameter is obtained.

When the silicon-oxide-coated zinc oxide is immersed in an aqueous solution having a hydrogen-ion exponent (pH) of 5 for one hour so that the content thereof reaches 0.05% by mass, the elution ratio of zinc being eluted in the aqueous solution is preferably 20% by mass or less, more preferably 10% by mass or less, and still more preferably 5% by mass or less.

The reasons for setting the elution ratio of zinc to 20% by mass or less is that, when the elution ratio of zinc exceeds 20 mass %, the stability of the silicon-oxide-coated zinc oxide degrades, in a case in which the silicon-oxide-coated zinc oxide is applied to a cosmetic, zinc ions being eluted react with a water-soluble macromolecule or the like such as an organic ultraviolet ray-screening agent or a viscosity improver, and the degradation of performance as a cosmetic, discoloration, a change in the viscosity, and the like are caused, which is not preferable.

In the silicon-oxide-coated zinc oxide, the decomposition ratio of Brilliant Blue generated by the photocatalytic activity of the zinc oxide particles is preferably 3% or less, more preferably 2% or less, and still more preferably 1% or less.

The reason for setting the decomposition ratio of Brilliant Blue generated by the photocatalytic activity of the zinc oxide particles to 3% or less is that, when the decomposition ratio of Brilliant Blue is 3% or less, the photocatalytic activity of the zinc oxide particles is suppressed, and thus the uniformity of the silicon oxide coating covering the zinc oxide particles is also high.

Meanwhile, in a case in which the decomposition ratio of Brilliant Blue exceeds 3%, the photocatalytic activity of the zinc oxide particles is not suppressed, and thus the surfaces of the zinc oxide particles are partially covered with the silicon oxide coating, and the uniformity of the silicon oxide coating becomes low.

The method for measuring the decomposition ratio of Brilliant Blue is as described below.

First, an aqueous solution of Brilliant Blue prepared so as to have a predetermined content ratio (for example, 5 ppm) of Brilliant Blue is produced, a predetermined amount of the aqueous solution of Brilliant Blue is sampled and put into a screw tube, and 1% by mass of the silicon-oxide-coated zinc oxide with respect to the mass of the aqueous solution in terms of zinc oxide is injected into the sampled aqueous solution of Brilliant Blue, and is ultrasonically dispersed, thereby preparing a suspension. Next, ultraviolet rays having a predetermined wavelength are radiated to the suspension from a predetermined distance (for example, 10 cm) for a predetermined time (for example, six hours).

As a lamp for radiating the ultraviolet rays, for example, a bactericidal lamp GL20 (with a wavelength of 253.7 nm and an ultraviolet ray output of 7.5 W, manufactured by Toshiba Corporation) can be used.

Next, the supernatant solution is sampled from the suspension exposed to ultraviolet radiation, the respective absorptiometric spectra of the aqueous solution of Brilliant Blue and the supernatant solution are obtained using atomic absorption spectrometry, and the decomposition ratio D of Brilliant Blue is computed using these measurement values from Expression (1) described below.

$$D=(A0-A1)/A0 \quad (2)$$

(Here, A0 represents the absorbance of the aqueous solution of Brilliant Blue (5 ppm) at the absorption maximum wavelength (630 nm) of the absorptiometric spectrum, and A1 represents the absorbance of the supernatant solution at the absorption maximum wavelength of the absorptiometric spectrum.)

Hereinafter, individual constituent elements of the silicon-oxide-coated zinc oxide of the second embodiment will be described in detail.

Zinc Oxide Particles

Zinc oxide particles are the same as those according to the first embodiment.

Silicon Oxide Coating

The silicon oxide coating is not particularly limited as long as the silicon oxide coating has a high degree of condensation so that "when the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$", which will be described below, are satisfied, and has high uniformity so that the decomposition ratio of Brilliant Blue generated by the photocatalytic activity of the zinc oxide particles reaches 3% or less.

The degree of condensation of silicon oxide can be easily determined by obtaining the NMR spectrum of a silicon-oxide-coated zinc oxide using solid-state $^{29}$Si MAS-nuclear magnetic resonance (NMR) spectroscopy and measuring the area ratios of signals attributed to individual environments of $Q^0$, $Q^1$, $Q^2$, $Q^3$, and $Q^4$ from the peak area ratios of the NMR spectrum.

Here, $Q^n$ (n=0 to 4) indicates a chemical structure determined depending on the number of bridging oxygen atoms, that is, oxygen atoms that bond two Si atoms, out of oxygen atoms in a $SiO_4$ tetrahedral unit which is a constituent unit of silicon oxide.

The area ratios of the signals attributed to these respective environments of $Q^0$, $Q^1$, $Q^2$, $Q^3$, and $Q^4$ are marked as $Q^0$, $Q^1$, $Q^2$, $Q^3$, and $Q^4$. Here, $Q^0+Q^1+Q^2+Q^3+Q^4=1$.

When the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$.

Here, in a case in which $Q^3+Q^4 \geq 0.6$ is satisfied, but $Q^4/(Q^3+Q^4)$ is smaller than 0.5 ($Q^4/(Q^3+Q^4)<0.5$) or in a case in which $Q^4/(Q^3+Q^4) \geq 0.5$ is satisfied, but $Q^3+Q^4$ is smaller than 0.6 ($Q^3+Q^4<0.6$), silicon oxide in the silicon oxide coating does not sufficiently condense, and thus a dense coating cannot be obtained, and consequently, there is a concern that the effect of suppressing the elution of zinc ions in the silicon-oxide-coated zinc oxide may not be sufficiently obtained, which is not preferable.

The uniformity of the silicon oxide coating can be evaluated using the decomposition ratio of Brilliant Blue generated by the photocatalytic activity of the above-described zinc oxide particles.

Here, when the decomposition ratio of Brilliant Blue is 3% or less, the photocatalytic activity of the zinc oxide particles is suppressed, and thus the uniformity of the silicon oxide coating covering the zinc oxide particles also becomes high.

On the other hand, in a case in which the decomposition ratio of Brilliant Blue exceeds 3%, the photocatalytic activity of the zinc oxide particles is not suppressed, and thus the surfaces of the zinc oxide particles are partially covered with the silicon oxide coating, and the uniformity of the silicon oxide coating becomes low.

In the silicon-oxide-coated zinc oxides of the first and second embodiments, the surfaces thereof may be surface-treated with a silicone resin.

When the silicon-oxide-coated zinc oxide is surface-treated with a silicone resin, the affinity of the silicon-oxide-coated zinc oxide to an oil phase, particularly, a silicone oil, becomes high, and thus it becomes easy to blend the silicon-oxide-coated zinc oxide into a water-in-oil (W/O) type or oil-in-water (O/W) type cosmetic.

That is, when the silicon-oxide-coated zinc oxide formed by treating the surface thereof with a silicone resin is blended into an oil phase so as to produce a water-in-oil type or oil-in-water type cosmetic, it is possible to suppress the elution of zinc ions in the water-in-oil (W/O) type or oil-in-water (O/W) type cosmetic.

The silicone resin used for the surface treatment is not particularly limited as long as the silicone resin can be used as a cosmetic, and examples thereof include methyl hydrogen polysiloxane, dimethyl polysiloxane, methicone, hydrogen dimethicone, triethoxysilylethyl polydimethylsiloxyethyl dimethicone, triethoxysilylethyl polydimethylsiloxyethyl hexyl dimethicone, (acrylate/tridecyl acrylate/methacrylate triethoxysilylpropyl/methacrylate dimethicone) copolymers, triethoxycaprylylsilane, and the like. These silicone resins may be used singly, a mixture of two or more silicone resins may be used, or a copolymer of these silicone resins may be used.

The amount of the surface treatment of the silicone resin in the surface treatment may be appropriately adjusted depending on an oil phase being used, and, for example, the amount of the surface treatment thereof is preferably in a range of 1% by mass or more and 20% by mass or less and more preferably in a range of 3% by mass or more and 10% by mass or less in relation to the total mass of the silicon-oxide-coated zinc oxide.

Method for Manufacturing Silicon-Oxide-Coated Zinc Oxide

First Embodiment

A method for manufacturing the silicon-oxide-coated zinc oxide of a first embodiment is a method including a zinc oxide suspension production step of producing a zinc oxide suspension by suspending zinc oxide particles in a solvent, a reaction step of adding any one or more of alkoxysilanes and oligomers of an alkoxysilane which are decamers or lower oligomers, a catalyst, and water to the zinc oxide suspension and causing a reaction, and a thermal treatment step of thermally treating the obtained reaction product at a temperature in a range of 200° C. or more and 550° C. or less.

Zinc Oxide Suspension Production Step

This is a step of producing a zinc oxide suspension by suspending zinc oxide particles in a solvent.

Here, the solvent that suspends zinc oxide particles is not particularly limited as long as the solvent is capable of suspending zinc oxide particles, and, in addition to water, alcohols such as methanol, ethanol, 1-propanol, 2-propanol, 1-butanol, 2-butanol, and octanol, esters such as ethyl acetate, butyl acetate, ethyl lactate, propylene glycol monomethyl ether acetate, propylene glycol monoethyl ether acetate, and γ-butyrolactone, and ethers such as diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, and diethylene glycol monoethyl ether can be preferably used.

In addition, ketones such as acetone, methyl ethyl ketone, methyl isobutyl ketone, acetyl acetone, and cyclohexanone, aromatic hydrocarbons such as benzene, toluene, xylene, and ethyl benzene, and amides such as dimethylformamide, N,N-dimethylacetoacetamide, and N-methyl pyrrolidone can be preferably used.

These solvents may be used singly, or a mixture of two or more solvents may be used.

The content ratio of the zinc oxide particles in the zinc oxide suspension is preferably in a range of 1% by mass or more and 80% by mass or less, more preferably in a range of 20% by mass or more and 70% by mass or less, and still more preferably in a range of 30% by mass or more and 60% by mass or less.

The reasons for setting the content ratio of the zinc oxide particles in the zinc oxide suspension in a range of 1% by mass or more and 80% by mass or less are as described below. When the content ratio of the zinc oxide particles is less than 1% by mass, it is necessary to remove a large amount of the solvent compared with the content of the zinc oxide particles in the suspension, and there is a concern of an increase in cost. On the other hand, when the content ratio exceeds 80% by mass, the viscous property of the suspension increases (the suspension becomes more viscous), and thus the dispersion stability of the zinc oxide particles degrades, and there is a concern that the zinc oxide particles may easily settle out.

Regarding the method for suspending the zinc oxide particles in the solvent, there is no particular limitation, and a well-known suspension method can be used. For example, a beads mill in which media such as zirconia beads are used, a ball mill, a homogenizer, a disper, a stirrer, or the like can be preferably used. The time necessary for a suspension treatment needs to be a sufficient time for the zinc oxide particles to be uniformly suspended in the solvent.

In this case, a dispersant may be added as necessary.

Reaction Step

This is a step of adding any one or more of alkoxysilanes and oligomers of an alkoxysilane which are decamers or lower oligomers, a catalyst, and water to the zinc oxide suspension and stirring the components for approximately 30 minutes to 24 hours, thereby causing a reaction.

The reason for limiting the component to be added to alkoxysilanes and oligomers of an alkoxysilane which are decamers or lower oligomers is to obtain a dense silicon oxide coating having a high degree of condensation of silicon oxide.

In a case in which an alkaline silicate metallic salt is used instead of the alkoxysilane, it is difficult to improve the degree of condensation of silicon oxide in the silicon oxide coating, and a dense silicon oxide coating cannot be obtained, which is not preferable.

In addition, the reasons for limiting the oligomers of an alkoxysilane to decamers or lower oligomers of an alkoxysilane are that, when the chain length of the oligomer becomes long, the distance between the oligomers becomes easily opened, and, in the case of an undecamer or a higher oligomer, even when a thermal treatment is carried out after the zinc oxide particles are coated, silicon oxide in the coating does not sufficiently condense, and thus a dense silicon oxide coating cannot be obtained, and there is a concern that a desired elution-suppressing effect may not be obtained.

The alkoxysilane is preferably a tetraalkoxysilane, and the oligomer of an alkoxysilane which is a decamer or a lower oligomer is preferably an oligomer of a tetraalkoxysilane which is a decamer or a lower oligomer.

The tetraalkoxysilane is expressed by General Formula (3) described below:

$$Si(OR)_4 \quad (3)$$

(Here, R represents an alkoxyl group (RO group), and these four alkoxyl groups (RO groups) may be all identical to each other or may be partially or all different from each other). The number of carbon atoms in the alkoxyl group is preferably in a range of 1 to 8.

Examples of the tetraalkoxysilane include tetramethoxysilane, tetraethoxysilane, tetra-n-propoxysilane, tetraisopropoxysilane, tetra-n-butoxysilane, tetraisobutoxysilane, tetra-sec-butoxysilane, tetra-t-butoxysilane, tetraphenoxysilane, monoethoxytrimethoxysilane, monobutoxytrimethoxysilane, monopentoxytrimethoxysilane, monohexoxytrimethoxysilane, dimethoxydiethoxysilane, dimethoxydibutoxysilane, and the like.

Among these, tetramethoxysilane and tetraethoxysilane can be preferably used since tetramethoxysilane and tetraethoxysilane have a high content of Si, the concentration thereof can be easily controlled when tetramethoxysilane and tetraethoxysilane are dispersed in the solvent, and tetramethoxysilane and tetraethoxysilane have a high hydrolysis and condensation reactivity.

These tetraalkoxysilanes may be used singly or a combination of two or more tetraalkoxysilanes may be used.

In addition, an oligomer of the tetraalkoxysilane which is a decamer or a lower oligomer can be obtained by adding water to monomers of one or more tetraalkoxysilanes and hydrolyzing and condensing the monomers to a certain extent.

Examples of commercially available products of the oligomer of the tetraalkoxysilane include MKC SILICATE MS51 (manufactured by Mitsubishi Chemical Corporation), METHYL SILICATE 51 (tetramer on average), METHYL SILICATE 53A (heptamer on average), ETHYL SILICATE 40 (pentamer on average), ETHYL SILICATE 48 (decamer on average) (all manufactured by Colcoat Co., Ltd.), and the like.

One or more of the tetraalkoxysilane and the oligomers of the tetraalkoxysilane which are decamers or lower oligomers are preferably added so that the content thereof falls in a range of 10% by mass or more and 45% by mass or less in relation to the zinc oxide particles in the zinc oxide suspension when converted to silicon oxide.

The catalyst is added for the purpose of accelerating the hydrolysis or condensation polymerization reaction of the tetraalkoxysilane and the oligomers of the tetraalkoxysilane which are decamers or lower oligomers. As the catalyst, a well-known acid catalyst or basic catalyst can be used (refer to Sumio Sakka's "Science of Sol-Gel Process" published by Agne Shofu Co., Ltd., Chapter 9 (p. 154 to p. 173)).

Examples of the acid catalyst include inorganic acids such as hydrochloric acid, sulfuric acid, nitric acid, and phosphoric acid; and organic acids such as formic acid, acetic acid, oxalic acid, lactic acid, and tartaric acid, and among these, an inorganic acid, in particular, hydrochloric acid can be preferably used. In addition, the acid catalysts may be used singly or a combination of two or more acid catalysts may be used.

Examples of basic catalysts include sodium hydroxide, potassium hydroxide, lithium hydroxide, cerium hydroxide, barium hydroxide, calcium hydroxide, pyridine, pyrrole, piperazine, pyrrolidine, piperidine, picoline, ammonia, methylamine, ethylamine, propylamine, butylamine, dimethylamine, diethylamine, dipropylamine, dibutylamine, trimethylamine, triethylamine, tripropylamine, tributylamine, monoethanolamine, diethanolamine, dimethylmonoethanolamine, monomethyldiethanolamine, triethanolamine, diazabicyclooctane, diazabicyclononane, diazabicycloundecene, urea, tetramethylammonium hydroxide, tetraethylammonium hydroxide, tetrapropylammonium hydroxide, tetrabutylammonium hydroxide, benzyltrimethylammonium hydroxide, choline, and the like.

Among these, ammonia, organic amines, and ammonium hydroxides can be preferably used. These basic catalysts may be used singly or a combination of two or more basic catalysts may be used.

As the catalyst, either the acid catalyst or the basic catalyst may be used, but the acid catalyst, which is an electrophilic reactant, can be preferably used.

The reaction temperature is not particularly limited as long as the hydrolysis or condensation polymerization reaction of the tetraalkoxysilane and the oligomers of the tetraalkoxysilane which are decamers or lower oligomers rapidly proceeds at the reaction temperature, but the reaction temperature is preferably in a range of 0° C. or more and 100° C. or less, more preferably in a range of 20° C. or more and 80° C. or less, and still more preferably in a range of 40° C. or more and 60° C. or less.

The amount of water added needs to be large enough to hydrolyze one or more of the tetraalkoxysilane and the oligomers of the tetraalkoxysilane which are decamers or lower oligomers, that is, to make the hydrolysis ratio reach 100% or greater.

As a result, the hydrolysis reaction of one or more of the alkoxysilane and the oligomers of the alkoxysilane which are decamers or lower oligomers proceeds, and a condensation reaction also proceeds, thereby obtaining a reaction liquid.

The reaction liquid is separated into solids and liquids through normal-pressure filtration, reduced-pressure filtration, pressurization filtration, centrifugal separation, or the like, thereby obtaining a solid-phase reaction product.

Thermal Treatment Step

This is a step of thermally treating the above-described reaction product at a temperature in a range of 200° C. or more and 550° C. or less.

The thermal treatment temperature of the reaction product is preferably in a range of 250° C. or more and 500° C. or less and more preferably in a range of 300° C. or more and 500° C. or less in order to accelerate the densification of the silicon oxide coating.

The reasons for limiting the thermal treatment temperature to a range of 200° C. or more and 550° C. or less are as described below. When the thermal treatment temperature is lower than 200° C., a dense silicon oxide coating that has been sufficiently condensed cannot be obtained, and consequently, there is a concern that an effect of suppressing the elution of zinc ions from the zinc oxide particles may not be sufficiently obtained. On the other hand, when the thermal treatment temperature exceeds 550° C., the silicon-oxide-coated zinc oxides having the silicon oxide coating formed thereon bond to each other, thus, coarse particles are formed or zinc oxide grains grow, and consequently, in a case in which a cosmetic into which the silicon-oxide-coated zinc oxide is blended is used, there is a concern that sufficient transparency may not be obtained in the visible light range.

In a case in which the surface of the silicon-oxide-coated zinc oxide obtained as described above is further surface-treated with a silicone resin, it is possible to use a well-known method such as a method (dry treatment method) in which the silicon-oxide-coated zinc oxide that has been subjected to the thermal treatment step and the silicone resin are directly mixed with each other or a method (wet treatment method) in which the silicon-oxide-coated zinc oxide that has been subjected to the thermal treatment step is dispersed in a solvent containing the silicone resin, then, the solvent is removed, and subsequently, a heating treatment is carried out.

In a case in which the silicon-oxide-coated zinc oxide that has been subjected to the thermal treatment step is dispersed in a solvent containing the silicone resin, the silicon-oxide-coated zinc oxide is preferably mixed with the solvent so that the content thereof falls in a range of 10% by mass or more and 40% by mass or less and is more preferably mixed with the solvent so that the content thereof falls in a range of 25% by mass or more and 35% by mass or less. When the silicon-oxide-coated zinc oxide is mixed with the solvent so that the content thereof falls in the above-described range, it is possible to improve the production efficiency.

The heating treatment is preferably carried out at a temperature in a range of 100° C. or more and 300° C. or less. When the heating treatment is carried out at a temperature in the above-described range, it is possible to surface-treat the surface of the silicon-oxide-coated zinc oxide with the silicone resin and to suppress the thermal decomposition of the silicone resin and the crystal growth of zinc oxide.

Through the above-described steps, the silicon-oxide-coated zinc oxide of the first embodiment can be produced.

Second Embodiment

A method for manufacturing the silicon-oxide-coated zinc oxide of a second embodiment is a method including a surface-modified zinc oxide suspension production step of producing a surface-modified zinc oxide suspension by suspending a surface-modified zinc oxide in a solvent, a reaction step of adding any one or more of alkoxysilanes and oligomers of an alkoxysilane which are decamers or lower oligomers, a catalyst, and water to the surface-modified zinc oxide suspension and causing a reaction, and a thermal treatment step of thermally treating the obtained reaction product at a temperature in a range of 200° C. or more and lower than 600° C.

Here, the surface-modified zinc oxide refers to a zinc oxide coated with a flexible silicon oxide layer which is capable of easily coating zinc oxide particles in a uniform manner.

The flexible silicon oxide layer may be a composite oxide of silicon oxide and a metallic oxide including 20% by mass or less of a metallic oxide such as aluminum oxide or titanium oxide in terms of the oxide.

The surface-modified zinc oxide used herein can be produced as described below.

3% by mass or more and 45% by mass or less of a silicon oxide layer in relation to zinc oxide particles having an average particle diameter in a range of 1 nm or more and 50 nm or less in terms of silicon oxide is formed on the surfaces of the zinc oxide particles using an water-based solution of an alkaline silicate metallic salt, thereby producing a surface-modified zinc oxide.

Here, the water-based solution of an alkaline silicate metallic salt refers to a water-based solution in which the alkaline silicate metallic salt is dissolved in a water-based solvent, and the water-based solvent refers to a solvent containing 50% by mass or more of water.

There is no particular limitation regarding a solvent other than water, but a polar solvent such as a water-soluble monovalent alcohol or a polyvalent alcohol is preferred in consideration of the compatibility with water.

There is no particular limitation regarding the alkaline silicate metallic salt, and it is possible to use a mixture of one or more selected from the group consisting of sodium orthosilicate salts, potassium orthosilicate salts, sodium mehasilicate salts, potassium mehasilicate salts, and silicate of soda.

Here, first, an amount of a water-based solution of an alkaline silicate metallic salt is prepared such that 3% by mass or more and 45% by mass or less of a silicon oxide layer in relation to zinc oxide particles in terms of silicon oxide can be generated, zinc oxide particles having an average particle diameter in a range of 1 nm or more and 50 nm or less are added to the water-based solution of an alkaline silicate metallic salt, and the components are stirred together, thereby producing a zinc oxide particle-containing suspension.

When a water-soluble compound of aluminum or titanium such as sodium aluminate, aluminum nitrate, aluminum sulfate, or titanyl sulfate is made to coexist with the zinc oxide particles in the water-based solution of an alkaline silicate metallic salt, it is possible to include aluminum oxide, titanium oxide, or the like to the silicon oxide layer.

Next, an acid such as hydrochloric acid is added to the zinc oxide particle-containing suspension so as to adjust the hydrogen-ion exponent (pH) of the zinc oxide particle-containing suspension in a range of 6 to 9, and the suspension is left to be still.

The reaction temperature is not particularly limited, but is preferably in a range of 40° C. or more and 100° C. or less and more preferably in a range of 50° C. or more and 70° C. or less in terms of the relationship with the precipitation rate of silicon oxide.

As a result, silicon oxide is precipitated on the surfaces of the zinc oxide particles included in the suspension, and a surface-modified zinc oxide having a silicon oxide layer formed on the surface is produced.

Next, the suspension is separated into solids and liquids, the obtained solid substance is washed using a solvent such as water, and furthermore, moisture is removed for the subsequent steps. There is no particular limitation regarding the method for removing moisture; however, generally, the solid substance is preferably dried at a temperature of 100° C. or higher. In addition, in a case in which moisture is removed at a low temperature of 80° C. or lower, reduced-pressure drying is preferred.

A dried substance obtained by removing moisture as described above may be further subjected to a thermal treatment step.

Surface-Modified Zinc Oxide Suspension Production Step

The surface-modified zinc oxide suspension production step is the same as the zinc oxide suspension production step in the first embodiment except for the fact that surface-modified zinc oxide is used instead of zinc oxide particles.

Reaction Step

This is a step of adding any one or more of alkoxysilanes and oligomers of an alkoxysilane which are decamers and lower oligomers, a catalyst, and water to the surface-modified zinc oxide suspension and stirring the components for approximately 30 minutes to 24 hours, thereby causing a reaction.

The reason for limiting the component to be added to alkoxysilanes and oligomers of an alkoxysilane which are decamers or lower oligomers is to obtain a dense silicon oxide coating having a high degree of condensation of silicon oxide.

In a case in which an alkaline silicate metallic salt or trialkoxysilane is used instead of the alkoxysilane, it is difficult to improve the degree of condensation of silicon oxide in the silicon oxide coating, and a dense silicon oxide coating cannot be obtained, which is not preferable.

In addition, the reasons for limiting the oligomers of an alkoxysilane to decamers or lower oligomers are that, when the chain length of the oligomer becomes long, the distance between the oligomers becomes easily opened, and, in the case of an undecamer or a higher oligomer, even when a thermal treatment is carried out after the surface-modified zinc oxide are coated, silicon oxide in the coating does not sufficiently condense, and thus a dense silicon oxide coating cannot be obtained, and there is a concern that a desired elution-suppressing effect may not be obtained.

The above-described alkoxysilane is the same as that according to the first embodiment.

In addition, the oligomers of the tetraalkoxysilane which are decamers or lower oligomers are the same as those according to the first embodiment.

One or more of the tetraalkoxysilane and the oligomers of the tetraalkoxysilane which are decamers or lower oligomers are preferably added so that the content thereof falls in a range of 5% by mass or more and 45% by mass or less in relation to the zinc oxide particles in the surface-modified zinc oxide suspension in terms of silicon oxide.

The catalyst is added for the purpose of accelerating the hydrolysis or condensation polymerization reaction of the tetraalkoxysilane and the oligomers of the tetraalkoxysilane which are decamers or lower oligomers. As the catalyst, a well-known acid catalyst or basic catalyst can be used (refer to Sumio Sakka's "Science of Sol-Gel Process" published by Agne Shofu Co., Ltd., Chapter 9 (p. 154 to p. 173)).

Examples of the acid catalyst are the same as those according to the first embodiment.

Examples of the basic catalyst are the same as those according to the first embodiment.

The reaction temperature is the same as that according to the first embodiment.

The amount of water added is the same as that according to the first embodiment.

As a result, the hydrolysis reaction of one or more of the tetraalkoxysilane and the oligomers of the tetraalkoxysilane which are decamers or lower oligomers proceeds, and a condensation reaction also proceeds, thereby obtaining a reaction liquid.

The reaction liquid is separated into solids and liquids through normal-pressure filtration, reduced-pressure filtration, pressurization filtration, centrifugal separation, or the like, thereby obtaining a solid-phase reaction product.

Thermal Treatment Step

This is a step of thermally treating the above-described reaction product at a temperature in a range of 200° C. or more and lower than 600° C.

The thermal treatment of the reaction product is preferably in a range of 250° C. or more and lower than 600° C. and more preferably in a range of 300° C. or more and 500° C. or less in order to accelerate the densification of the silicon oxide coating.

The reasons for limiting the thermal treatment temperature to a range of 200° C. or more and lower than 600° C. are as described below. When the thermal treatment temperature is lower than 200° C., a dense silicon oxide coating that has been sufficiently condensed cannot be obtained, and consequently, there is a concern that an effect of suppressing the elution of zinc ions from the zinc oxide particles may not be sufficiently obtained. On the other hand, when thermal treatment temperature is 600° C. or higher, the silicon-oxide-coated zinc oxides having the silicon oxide coating formed thereon bond to each other, thus, coarse particles are formed or zinc oxide grains grow, and consequently, in a case in which a cosmetic into which the silicon-oxide-coated zinc oxide is blended is used, there is a concern that sufficient transparency may not be obtained in the visible light range.

The case in which the surface of the silicon-oxide-coated zinc oxide obtained as described above is further surface-treated with a silicone resin is the same as that according to the first embodiment.

Through the above-described steps, the silicon-oxide-coated zinc oxide of the second embodiment can be produced.

Silicon-Oxide-Coated-Zinc-Oxide-Containing Composition

A silicon-oxide-coated-zinc-oxide-containing composition of the present embodiment includes the above-described silicon-oxide-coated zinc oxide and a solvent.

The average particle diameter of the silicon-oxide-coated zinc oxide is preferably in a range of 3 nm or more and 500 nm or less, more preferably in a range of 10 nm or more and 300 nm or less, and still more preferably in a range of 20 nm or more and 100 nm or less.

The reasons for limiting the average particle diameter of the silicon-oxide-coated zinc oxide to the above-described range are as described below. When the average particle diameter thereof is smaller than 3 nm, the particle diameters are too small, the surface energy of the silicon-oxide-coated zinc oxide is high, thus, the zinc oxide particles easily agglomerate together, and it becomes difficult to maintain a silicon-oxide-coated zinc oxide having a desired form and size. On the other hand, when the average particle diameter exceeds 500 nm, the transparency of the silicon-oxide-coated zinc oxide is likely to degrade, and, in a case in which the silicon-oxide-coated-zinc-oxide-containing composition is used for a cosmetic or the like, there is a concern that transparency in the visible light range may be impaired or friction or the like may be caused and thus the feeling during the use of the cosmetic or the like may deteriorate.

The average dispersed particle diameter of the silicon-oxide-coated zinc oxide in the silicon-oxide-coated-zinc-oxide-containing composition is preferably in a range of 10 nm or more and 1 µm or less, more preferably in a range of 20 nm or more and 800 nm or less, and still more preferably in a range of 25 nm or more and 500 nm or less.

The content ratio of the silicon-oxide-coated zinc oxide in the silicon-oxide-coated-zinc-oxide-containing composition may be appropriately adjusted in order to obtain desired ultraviolet ray-screening performance, and is not particularly limited, but the content ratio thereof is preferably in a range of 1% by mass or more and 80% by mass or less, more preferably in a range of 20% by mass or more and 70% by mass or less, and still more preferably in a range of 30% by mass or more and 60% by mass or less.

The reasons for limiting the content ratio of the silicon-oxide-coated zinc oxide to a range of 1% by mass or more and 80% by mass or less are as described below. When the content ratio of the silicon-oxide-coated zinc oxide is less than 1% by mass, there is a concern that the composition may become incapable of exhibiting a sufficient ultraviolet ray-screening function, thus, when this composition is blended into a cosmetic or the like, it is necessary to add a large amount of the composition in order to exhibit a desired ultraviolet ray-screening function, and there is a concern that the manufacturing cost may become high, which is not preferable. On the other hand, when the content ratio exceeds 80% by mass, the viscous property of the composition increases, and thus the dispersion stability of the silicon-oxide-coated zinc oxide degrades, and there is a concern that the silicon-oxide-coated zinc oxide may easily settle out, which is not preferable.

Here, the solvent is not particularly limited as long as the solvent is capable of dispersing the silicon-oxide-coated zinc oxide, and, for example, water, alcohols such as methanol, ethanol, 1-propanol, 2-propanol, 1-butanol, 2-butanol, and octanol, glycerin, esters such as ethyl acetate, butyl acetate, ethyl lactate, propylene glycol monomethyl ether acetate, propylene glycol monoethyl ether acetate, and γ-butyrolactone, and ethers such as diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, and diethylene glycol monethyl ether can be preferably used.

In addition, ketones such as acetone, methyl ethyl ketone, methyl isobutyl ketone, acetyl acetone, and cyclohexanone; aromatic hydrocarbons such as benzene, toluene, xylene, and ethyl benzene;

cyclic hydrocarbons such as cyclohexaene; amides such as dimethylformamide, N,N-dimethylacetoacetamide, and N-methyl pyrrolidone; and chain-like polysiloxanes such as dimethylpolysiloxane, methylphenylpolysiloxane, and diphenylpolysiloxane can also be preferably used.

In addition, cyclic polysiloxanes such as octamethylcyclotetrasiloxane, decamethylcyclopentasiloxane, and dodecamethylcyclohexanesiloxane; and modified polysiloxanes such as amino-modified polysiloxane, polyether-modified polysiloxane, alkyl-modified polysiloxane, and fluorine-modified polysiloxane can also be preferably used.

These may be used singly, or a mixture of two or more solvents may be used.

The silicon-oxide-coated-zinc-oxide-containing composition of the present embodiment may include ordinarily-used additives such as a dispersant, a stabilizer, a water-soluble binder, and a viscosity improver as long as the characteristics thereof are not impaired.

As the dispersant, an anionic surfactant, a cationic surfactant, an amphoteric surfactant, a non-ionic surfactant, a silane coupling agent such as an organoalkoxysilane or organochlorosilane, or a modified silicone such as a polyether-modified silicone or an amino-modified silicone is preferably used. The kind and amount of the dispersant may be appropriately selected depending on the particle diameters of complex particles and the kind of the target dispersion medium, and the dispersant may be used singly or a mixture of two or more dispersants may be used.

As the water-soluble binder, a polyvinyl alcohol (PVA), polyvinyl pyrrolidone, hydroxycellulose, polyacrylic acid, or the like can be used.

Regarding the viscosity improver, in a case in which the silicon-oxide-coated-zinc-oxide-containing composition is applied to a cosmetic, there is no particular limitation as long as the viscosity improver is a viscosity improver used for cosmetics. Examples of the viscosity improver that can be preferably used include natural water-soluble macromolecules such as gelatin, casein, collagen, hyaluronic acid, albumin, and starch, semisynthetic macromolecules such as methyl cellulose, ethyl cellulose, methylhydroxypropyl cellulose, carboxymethyl cellulose, hydroxymethylcellulose, hydroxypropyl cellulose, sodium carboxymethyl cellulose, and propylene glycol alginate ester, synthetic macromolecules such as polyvinyl alcohol, polyvinyl pyrrolidone, carbomers (carboxy vinyl polymer), polyacrylate, and polyethylene oxide, inorganic minerals such as bentonite, laponite, and hectorite. The viscosity improvers may be used singly or a combination of two or more viscosity improvers may be used.

Among these viscosity improvers, the synthetic macromolecule is preferred, and a carbomer is more preferred.

Here, in a case in which a carbomer is used as the viscosity improver, the content ratio of the carbomer in the silicon-oxide-coated-zinc-oxide-containing composition is preferably in a range of 0.01% by mass or more and 10% by mass or less and more preferably in a range of 0.01% by mass or more and 3% by mass or less.

When the content ratio of the carbomer in the silicon-oxide-coated-zinc-oxide-containing composition is lower than 0.01% by mass, there is a concern that a viscosity-improving effect may not be obtained, and, on the other hand, when the content ratio of the carbomer exceeds 10% by mass, the viscosity becomes too high, which is not preferable from the viewpoint of use.

In addition, in a case in which a carbomer is used as the viscosity improver, the hydrogen-ion exponent (pH) of the silicon-oxide-coated-zinc-oxide-containing composition is preferably in a range of 5 or more and 10 or less, more preferably in a range of 6 or more and 10 or less, and still more preferably in a range of 7 or more and 9 or less. When the pH of the silicon-oxide-coated-zinc-oxide-containing composition is set in the above-described range, it is possible to suppress a change in the viscosity and the like over time.

Meanwhile, carbomers (carboxy vinyl polymer) are widely used as a viscosity improver for water-based cosmetics, but the carbomer improves the viscosity (makes the composition gelate) using the interaction between carboxyl groups or between carboxylate groups, and thus the presence of zinc ions breaks the network structure of the carbomer and disables the maintenance of a constant viscous property. Therefore, when several percent by mass of zinc oxide is mixed into an aqueous solution of a carbomer having an adjusted viscosity, the viscosity decreases within several hours.

In addition, even in a case in which zinc oxide having a surface activity suppressed by coating the surface with an inorganic oxide or a resin is used, in many cases, the viscosity decreases or phases separate within several hours to several days. Therefore, in a case in which a carbomer and zinc oxide are jointly used, there is a requirement to suppress or reduce a decrease in the viscosity of a mixture including a carbomer and zinc oxide.

In addition, in a case in which a decrease in the viscosity of an aqueous solution of a carbomer is suppressed using zinc oxide having a surface activity suppressed by coating the surface with an inorganic oxide or a resin of the related art, there is a frequent significant problem of a decrease in the viscosity after a certain period of time elapses rather than a decrease in the viscosity in the initial phase.

The decrease in the viscosity in the initial phase can be coped with by, for example, setting the viscosity of the aqueous solution of a carbomer to be high in advance; however, when the viscosity changes in the middle to long term after a certain period of time elapses, the properties of cosmetics change during the distribution of the cosmetics, and the stability over time is impaired. Particularly, zinc oxide having a surface treated with an inorganic oxide or a resin has a certain degree of an elution-suppressing effect, and thus there has been a concern that zinc ions may be gradually eluted in the middle to long term.

In addition, in the related art, there have been only a small number of reported cases regarding the change of the viscosity of a composition including a carbomer, and, even in the reported cases, only an effect of suppressing a change in the viscosity over time at room temperature for approximately seven days has been confirmed.

In the silicon-oxide-coated-zinc-oxide-containing composition of the present embodiment, since a silicon-oxide-coated zinc oxide having a stronger zinc elution-suppressing effect than zinc oxide coated with an inorganic oxide or a resin of the related art is used, even when a carbomer is used as the viscosity improver, the viscosity decreases only slightly over time, and it is possible to obtain a composition having excellent product stability.

In the silicon-oxide-coated-zinc-oxide-containing composition of the present embodiment, the value obtained by dividing the viscosity under acceleration conditions, for example, the viscosity after 300 hours in a case in which the composition is stored at 40° C., by the viscosity after the decrease in the viscosity in the initial phase, for example, the viscosity after 15 hours is preferably in a range of 0.8 or more and 1.2 or less.

As described above, when the value obtained by dividing the viscosity after 300 hours under acceleration conditions by the viscosity after the decrease in the viscosity in the initial phase is set in the above-described range, it is possible to maintain the viscosity of the silicon-oxide-coated-zinc-oxide-containing composition in the middle to long term.

In the silicon-oxide-coated-zinc-oxide-containing composition of the present embodiment, in a case in which the content ratio of the silicon-oxide-coated zinc oxide is set to 15% by mass and a 32 μm-thick coating is produced using the composition, the transmission of light having a wavelength of 450 nm is preferably 50% or higher, more preferably 60% or higher, and still more preferably 70% or higher.

The transmission can be obtained by applying the silicon-oxide-coated-zinc-oxide-containing composition containing 15% by mass of the silicon-oxide-coated zinc oxide onto a silica substrate using a bar coater so as to form a 32 μm-thick coating, and obtaining the spectral transmission of the coating using a SPF analyzer UV-1000S (manufactured by Labsphere, Inc.).

The method for manufacturing the silicon-oxide-coated-zinc-oxide-containing composition of the present embodiment is not particularly limited as long as the silicon-oxide-coated zinc oxide can be dispersed in the above-described solvent.

As the above-described dispersion method, a well-known dispersion method can be used. For example, in addition to a stirrer, a beads mill in which zirconia beads are used, a ball mill, a homogenizer, an ultrasonic disperser, a kneader, a three roll mill, a rotation-revolution mixer, or the like can be preferably used.

The time necessary for a dispersion treatment needs to be a sufficient time for the silicon-oxide-coated zinc oxide to be uniformly dispersed in the solvent.

Next, as specific examples of the silicon-oxide-coated-zinc-oxide-containing composition of the present embodiment, (1) a silicon-oxide-coated-zinc-oxide-containing silicone resin-based composition in which the silicon-oxide-coated zinc oxide is dispersed in a silicone resin that is a non-water-soluble dispersion medium and (2) a silicon-oxide-coated-zinc-oxide-containing water-based composition in which the silicon-oxide-coated zinc oxide is dispersed in water will be respectively described.

Silicon-Oxide-Coated-Zinc-Oxide-Containing Silicone Resin-Based Composition

The silicon-oxide-coated-zinc-oxide-containing silicone resin-based composition is a silicone resin-based composition in which the silicon-oxide-coated zinc oxide is dispersed in a silicone resin, in which the content ratio of the silicon-oxide-coated zinc oxide is set in a range of 1% by mass or more and 80% by mass or less, more preferably set in a range of 20% by mass or more and 70% by mass or less, and still more preferably in a range of 30% by mass or more and 60% by mass or less.

The average dispersed particle diameter of the silicon-oxide-coated zinc oxide in the silicon-oxide-coated-zinc-oxide-containing silicone resin-based composition is preferably in a range of 10 nm or more and 1 μm or less, more preferably in a range of 20 nm or more and 800 nm or less, and still more preferably in a range of 25 nm or more and 500 nm or less.

In the present embodiment, a silicon-oxide-coated zinc oxide surface-treated with a silicone is more preferably used.

The silicone resin is not particularly limited as long as the silicone resin can be used in a cosmetic, and, for example, a cyclic silicone resin, a straight-chain silicone resin, or the like can be used.

Examples of the silicone resin include straight-chain siloxanes such as dimethyl polysiloxane, methyl phenyl polysiloxane, diphenyl polysiloxane, and methyl hydrogen polysiloxane, cyclic siloxanes such as hexamethylcyclotrisiloxane, octamethylcyclotetrasiloxane, decamethyl pentasiloxane, decamethylcyclopentasiloxane, dodecamethylcyclohexanesiloxane, and tetramethyltetrahydrogen polysiloxane, modified silicones such as amino-modified silicone, polyether-modified silicone, alkyl-modified silicone, methyl trimethicone, and the like.

These silicone resins may be used singly or a mixture of two or more silicone resins may be used.

The silicon-oxide-coated-zinc-oxide-containing silicone resin-based composition may include a dispersant.

Examples of the dispersant include modified silicones such as polyether-modified silicone, polyglycerin-modified silicone, amino-modified silicone, phenyl-modified silicone, alkyl-modified silicone, carbinol-modified silicone, and dimethyl silicone, surfactants such as an anionic surfactant, a cationic surfactant, an amphoteric surfactant, and a non-ionic surfactant, and silane coupling agents such as an organoalkoxysilane and organochlorosilane.

These dispersants may be used singly or a mixture of two or more dispersants may be used.

The amount of the dispersant added is preferably in a range of 1% by mass or more and 50% by mass or less in relation to the mass of the silicon-oxide-coated zinc oxide in the silicon-oxide-coated-zinc-oxide-containing silicone resin-based composition.

When the amount of the dispersant added is adjusted to be in the above-described range, even in a case in which the silicon-oxide-coated-zinc-oxide-containing silicone resin-based composition is used singly or is directly mixed into a cosmetic, it is possible to sufficiently ensure transparency in a case in which the composition is applied and spread onto the skin.

In addition, into the silicon-oxide-coated-zinc-oxide-containing silicone resin-based composition, a natural oil, a moisturizing agent, a viscosity improver, a perfume, a preservative, and the like may be further mixed as long as the characteristics of the composition are not impaired.

The silicon-oxide-coated-zinc-oxide-containing silicone resin-based composition may also be made into an oil phase, be emulsified with an aqueous component, and thus be made into an emulsified composition.

The oil phase preferably contains at least one of a higher alcohol and a higher fatty acid and more preferably contains both a higher alcohol and a higher fatty acid. When these components are contained in the oil phase, a firm skin feeling and a moisturized feeling improve, and the sustainability of these effects improves.

The higher alcohol is not particularly limited as long as the higher alcohol can be used as a cosmetic. For example, capryl alcohol, lauryl alcohol, stearyl alcohol, oleyl alcohol, myristyl alcohol, cetyl alcohol, cholesterol, phytosterol, and the like can be preferably used. These may be used singly or a combination of two or more higher alcohols may be used.

As the higher fatty acid, a saturated or unsaturated fatty acid having 12 to 24 carbon atoms is preferably used, and, for example, myristic acid, palmitic acid, stearic acid, isostearic acid, linoleic acid, arachidonic acid, and the like are preferably used. These may be used singly or a combination of two or more higher fatty acids may be used.

Into this oil phase, an oil-soluble preservative, an ultraviolet absorber, an oil-soluble chemical, an oil-soluble pigment, an oil-soluble protein, a vegetable oil, an animal oil, and the like may be appropriately mixed as necessary.

The method for manufacturing the silicon-oxide-coated-zinc-oxide-containing silicone resin-based composition is not particularly limited as long as it is possible to disperse the silicon-oxide-coated zinc oxide in the silicone resin.

As the above-described dispersion method, a well-known dispersion device can be used. As the above-described dispersion device, for example, a stirrer, a beads mill, a ball mill, a homogenizer, an ultrasonic disperser, a kneader, a three roll mill, a rotation-revolution mixer, or the like can be preferably used.

The time necessary for a dispersion treatment needs to be a sufficient time for the silicon-oxide-coated zinc oxide to be uniformly dispersed in the silicone resin.

Silicon-Oxide-Coated-Zinc-Oxide-Containing Water-Based Composition

The silicon-oxide-coated-zinc-oxide-containing water-based composition is a water-based composition formed by dispersing the silicon-oxide-coated zinc oxide in a water-based dispersion medium including alcohols, in which the content ratio of the silicon-oxide-coated zinc oxide is set in a range of 1% by mass or more and 80% by mass or more, more preferably set in a range of 20% by mass or more and 70% by mass or less, and still more preferably in a range of 30% by mass or more and 60% by mass or less, and 5% by mass or more and 20% by mass or less of a water-based dispersion medium containing an alcohol is included.

The average dispersed particle diameter of the silicon-oxide-coated zinc oxide in the silicon-oxide-coated-zinc-oxide-containing water-based composition is preferably in a range of 10 nm or more and 1 μm or less, more preferably in a range of 20 nm or more and 800 nm or less, and still more preferably in a range of 25 nm or more and 500 nm or less.

Here, the water-based dispersion medium containing an alcohol is a dispersion medium including an alcohol and water, and examples of the alcohol include monovalent or polyvalent alcohols having 1 to 6 carbon atoms such as ethanol, 1-propanol, 2-propanol, 1-butanol, 2-butanol, octanol, glycerin, 1,3-butylene glycol, propylene glycol, and sorbitol. Among these, monovalent alcohols are preferred, and ethanol is particularly preferred.

In a case in which the water-based composition is made up of the silicon-oxide-coated zinc oxide and the water-based dispersion medium including the alcohol, the content ratio of the alcohol is preferably in a range of 5% by mass or more and 20% by mass or less, and more preferably in a range of 10% by mass or more and 20% by mass or less.

Particularly, in a case in which the content ratio of the alcohol is set in a range of 10% by mass or more and 20% by mass or less, it is possible to improve the dispersibility and the aging stability of the silicon-oxide-coated zinc oxide in the water-based composition, which is preferable.

The silicon-oxide-coated-zinc-oxide-containing water-based composition may further include a water-soluble macromolecule in a range of 0.001% by mass or more and 10% by mass or less, more preferably in a range of 0.005% by mass or more and 5% by mass or less, and still more preferably in a range of 0.01% by mass or more and 3% by mass or less. In this case, it is necessary to adjust the content ratios of the respective components so that the total of the respective content ratios of the silicon-oxide-coated zinc oxide, the water-based dispersion medium including an alcohol, and the water-soluble macromolecule does not exceed 100% by mass.

In a case in which the silicon-oxide-coated-zinc-oxide-containing water-based composition is applied to a cosmetic, the water-soluble macromolecule included in the water-based composition is not particularly limited as long as the macromolecule can be used in cosmetic use, and examples thereof include gum arabic, sodium alginate, casein, carrageenan, galactan, carboxyvinyl polymers, carboxymethyl cellulose, sodium carboxymethyl cellulose, carboxymethyl starch, agar, xanthan gum, quince seed, guar gum, collagen, gelatin, cellulose, dextran, dextrin, gum tragacanth, hydroxyethyl cellulose, hydroxypropyl cellulose, sodium hyaluronate pectin, pullulan, methyl cellulose, and methyl hydroxypropyl cellulose. These water-soluble macromolecules may be used singly, or a mixture of two or more water-soluble macromolecules may be used.

The water-soluble macromolecule plays roles as a dispersant and a viscosity adjuster, and, when added to the water-based composition, also improves the dispersibility and the aging stability of the silicon-oxide-coated zinc oxide in the water-based composition.

In a case in which the water-based composition includes the water-soluble macromolecule, the content ratio of the alcohol is preferably in a range of 5% by mass or more and 20% by mass or less and more preferably in a range of 15% by mass or more and 20% by mass or less.

The reasons for setting the content ratio of the alcohol in a range of 5% by mass or more and 20% by mass or less in a case in which the water-based composition includes the water-soluble macromolecule are as described below. When the content ratio thereof is lower than 5% by mass, the content of the alcohol is too small, and thus the water-soluble macromolecule cannot uniformly infiltrate into the alcohol and unevenly swells due to moisture, and consequently, the dispersibility of the silicon-oxide-coated zinc oxide degrades, handling becomes difficult, and furthermore, the aging stability of the water-based composition degrades, which is not preferable.

In addition, when the content ratio thereof exceeds 20% by mass, the viscous property of the entire water-based composition becomes high, the dispersion stability of the silicon-oxide-coated zinc oxide degrades, and the aging stability of the water-based composition also degrades, which is not preferable.

The silicon-oxide-coated-zinc-oxide-containing water-based composition can be obtained by mixing the silicon-oxide-coated zinc oxide into the water-based dispersion medium including the alcohol or the water-based dispersion medium including the alcohol and the water-soluble macromolecule, and then mixing water into the mixture so as to disperse the above-described components. The amount of water may be appropriately adjusted and is preferably in a range of 15% by mass or more and 94% by mass or less in consideration of the dispersion stability and aging stability of the silicon-oxide-coated zinc oxide.

When the amount of water is adjusted to be in the above-described range, it is possible to obtain a silicon-oxide-coated-zinc-oxide-containing water-based composition in which, even in a case in which the composition is used singly or is mixed into a cosmetic, it is possible to sufficiently ensure transparency in a case in which the composition is applied and spread onto the skin.

The silicon-oxide-coated-zinc-oxide-containing water-based composition may also be made into a water phase and be made into an emulsified composition in which an oil phase and the water phase are mixed together.

Cosmetic

A cosmetic of the present embodiment includes either or both the above-described silicon-oxide-coated zinc oxide and the above-described silicon-oxide-coated-zinc-oxide-containing composition in a base.

In a case in which the silicon-oxide-coated zinc oxide is used for an ultraviolet ray-screening use, the average particle diameter of the silicon-oxide-coated zinc oxide is preferably in a range of 3 nm or more and 500 nm or less, more preferably in a range of 10 nm or more and 300 nm or less, and still more preferably in a range of 20 nm or more and 100 nm or less.

In addition, in a case in which the silicon-oxide-coated-zinc-oxide-containing composition is used for an ultraviolet ray-screening use, the average particle diameter of the silicon-oxide-coated zinc oxide included in the silicon-oxide-coated-zinc-oxide-containing composition is preferably in a range of 3 nm or more and 500 nm or less, more preferably in a range of 10 nm or more and 300 nm or less, and still more preferably in a range of 20 nm or more and 100 nm or less.

The average dispersed particle diameter of the silicon-oxide-coated zinc oxide included in the cosmetic is preferably in a range of 10 nm or more and 1 µm or less, more preferably in a range of 20 nm or more and 800 nm or less, and still more preferably in a range of 25 nm or more and 500 nm or less.

The content ratio of the silicon-oxide-coated zinc oxide included in the cosmetic for which either or both the above-described silicon-oxide-coated zinc oxide and the above-described silicon-oxide-coated-zinc-oxide-containing composition are used may be appropriately adjusted, and the content ratio thereof is preferably in a range of 1% by mass or more and 60% by mass or less in relation to the mass of the entire cosmetic. When the content of the silicon-oxide-coated zinc oxide is in the above-described range, it is possible to sufficiently ensure transparency, and furthermore, a cosmetic having no rough feeling and the like and providing an excellent feeling during use can be obtained.

The cosmetic of the present embodiment may include additives and the like which are generally used for cosmetics such as organic ultraviolet ray-screening agents, inorganic ultraviolet ray-screening agents, and whitening agents as long as the effects of the present invention are not impaired.

Examples of the organic ultraviolet ray-screening agents include anthranilates, cinnamic acid derivatives, salicylic acid derivatives, camphor derivatives, benzophenone derivatives, β,β'-diphenylacrylate derivatives, benzotriazole derivatives, benzalmalonate derivatives, benzimidazole derivatives, imidazolines, bisbenzoazolyl derivatives, p-amino benzoic acid (PABA) derivatives, and methylene bis(hydroxyphenyl benzotriazole) derivatives, and it is possible to selectively use one or more selected from the above-described group.

In addition, examples of the inorganic ultraviolet ray-screening agents include oxides other than zinc oxide, for example, titanium oxide and cerium oxide, and it is possible to selectively use one or more selected from the above-described group.

The cosmetic can be obtained by blending the silicon-oxide-coated zinc oxide into a base such as an emulsion, a cream, a foundation, a lipstick, rouge, or eyeshadow as in the related art.

Furthermore, it is possible to obtain a water-based cosmetic having excellent ultraviolet ray-screening performance, transparent feeling, and feeling during use by blending the silicon-oxide-coated zinc oxide into a water-based cosmetic such as a facial lotion or a sunscreen gel for which formulation is difficult in the related art.

Furthermore, when this cosmetic is used as a component of a cosmetic product, it is possible to provide a variety of cosmetic products having excellent ultraviolet ray-screening performance, transparent feeling, and feeling during use such as a skincare cosmetic product, a makeup cosmetic product, and a body care cosmetic product. Particularly, the cosmetic is particularly preferable for the sun-screening and the like of a body care cosmetic product requiring ultraviolet ray-screening performance.

As described above, according to the silicon-oxide-coated zinc oxide of the first embodiment, when the surfaces of zinc oxide particles are coated with a silicon oxide coating, the average particle diameter of the zinc oxide particles is set in a range of 1 nm or more and 50 nm or less, and furthermore, when the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied, it is possible to suppress the elution of zinc ions from the zinc oxide particles to the outside due to the dense silicon oxide coating that coats the zinc oxide particles. Therefore, in a case in which the silicon-oxide-coated zinc oxide is applied to a cosmetic, it is possible to suppress the degradation of performance as a cosmetic, discoloration, a change in the viscosity, and the like which are caused by the elution of zinc ions.

According to the silicon-oxide-coated zinc oxide of the second embodiment, since the surfaces of zinc oxide particles are coated with a dense silicon oxide coating, the average particle diameter of the zinc oxide particles is in a range of 1 nm or more and 50 nm or less, furthermore, when the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are set to be satisfied, and the decomposition ratio of Brilliant Blue generated by the photocatalytic activity of the zinc oxide particles is set to 3% or less, the surfaces of zinc oxide particles are uniformly covered with a dense silicon oxide coating, and thus it is possible to suppress the elution of zinc ions from the zinc oxide particles to the outside. Therefore, in a case in which the silicon-oxide-coated zinc oxide is applied to a cosmetic, it is possible to suppress the degradation of performance as a cosmetic, discoloration, a change in the viscosity, and the like which are caused by the elution of zinc ions.

According to the method for manufacturing the silicon-oxide-coated zinc oxide of the first embodiment, since zinc oxide particles are suspended in a solvent so as to produce a zinc oxide suspension, next, anyone or more of alkoxysilanes and oligomers of an alkoxysilane which are decamers or lower oligomers, a catalyst, and water are added to and reacted with the zinc oxide suspension, and then the obtained reaction product is thermally treated at a temperature in a range of 200° C. or more and 550° C. or less, it is possible to produce silicon-oxide-coated zinc oxide capable of suppressing the elution of zinc ions from the zinc oxide particles.

According to the method for manufacturing the silicon-oxide-coated zinc oxide of the second embodiment, since 3% by mass or more and 45% by mass or less of a silicon oxide layer in relation to zinc oxide particles having an average particle diameter in a range of 1 nm or more and 50 nm or less in terms of silicon oxide is formed on the surfaces of the zinc oxide particles using an water-based solution of an alkaline silicate metallic salt so as to produce a surface-modified zinc oxide, next, the surface-modified zinc oxide is suspended in a solvent so as to produce a surface-modified zinc oxide suspension, next, any one or more of alkoxysilanes and oligomers of an alkoxysilane which are decamers or lower oligomers, a catalyst, and water are added to and reacted with the surface-modified zinc oxide suspension, and then the obtained reaction product is thermally treated at a temperature in a range of 200° C. or more and lower than 600° C., it is possible to uniformly cover the surfaces of the zinc oxide particles with a dense silicon oxide coating. Therefore, it is possible to produce silicon-oxide-coated zinc oxide capable of suppressing the elution of zinc ions from the zinc oxide particles.

According to the silicon-oxide-coated-zinc-oxide-containing composition of the present embodiment, since the composition includes the silicon-oxide-coated zinc oxide of the present embodiment and a solvent, it is possible to suppress the elution of zinc element included in the silicon-oxide-coated zinc oxide in the form of zinc ions to the outside. Therefore, it is possible to suppress the degradation of performance as a composition, discoloration, a change in the viscosity, and the like which are caused by the elution of zinc ions.

In the silicon-oxide-coated-zinc-oxide-containing composition, since the elution of zinc ions is suppressed, the silicon-oxide-coated-zinc-oxide-containing composition can be preferably used for cosmetics such as water-based dispersion bodies, oil-in-water (O/W) type dispersion bodies, water-in-oil (W/O) type dispersion bodies, and multilayer (W/O/W or O/W/O) type dispersion bodies, particularly for sun screening. In addition, in a case in which the silicon-oxide-coated-zinc-oxide-containing composition is applied to a resin film such as polyester or polyamide, it is also possible to preferably use the silicon-oxide-coated-zinc-oxide-containing composition as an ultraviolet ray-screening agent for resin films.

Furthermore, since it is possible to mix the silicon-oxide-coated-zinc-oxide-containing composition with a carbomer or an aqueous solution of a carbomer, it is possible to provide a water-soluble composition or a non-water-soluble composition having an excellent feeling during use.

According to the cosmetic of the present embodiment, since the cosmetic includes either or both the silicon-oxide-coated zinc oxide of the present embodiment and the silicon-oxide-coated-zinc-oxide-containing composition of the present embodiment in a base, it is possible to suppress the elution of zinc ions to the outside. Therefore, it is possible to suppress the degradation of performance as a cosmetic, discoloration, a change in the viscosity, and the like which are caused by the elution of zinc ions.

EXAMPLES

Hereinafter, the present invention will be specifically described using examples and comparative examples, but the present invention is not limited to these examples.

First Embodiment

Example 1

Zinc oxide particles (with an average particle diameter of 25 nm; manufactured by Sumitomo Osaka Cement Co., Ltd.) and methanol were mixed together and then were ultrasonically dispersed, thereby preparing a zinc oxide methanol suspension having a content ratio of zinc oxide of 12.5% by mass.

Next, methyl silicate 51 (manufactured by Colcoat Co., Ltd.), methanol, and water were mixed with the zinc oxide methanol suspension so that the total content thereof reached 10% by mass in relation to the zinc oxide particles in the zinc oxide methanol suspension in terms of silicon oxide. Next, 1 N hydrochloric acid was added to this liquid mixture, thereby producing a liquid mixture.

The content ratio of zinc oxide in this liquid mixture was 5% by mass, and the molar ratio between methyl silicate 51, pure water, and hydrochloric acid was 1:10:0.1.

Next, the liquid mixture was heated to 60° C., was held at this temperature for three hours, and was reacted.

After the reaction, solids and liquids were separated through centrifugal separation, and the obtained solid-phase reaction product was dried at 120° C., thereby obtaining a product A.

Next, the product A was thermally treated at 500° C. for two hours, thereby obtaining a silicon-oxide-coated zinc oxide of Example 1.

Example 2

A silicon-oxide-coated zinc oxide of Example 2 was obtained according to Example 1 except for the fact that the amount of the methyl silicate 51 (manufactured by Colcoat Co., Ltd.) was set to reach 20% by mass in relation to zinc oxide particles in terms of silicon oxide.

Example 3

A silicon-oxide-coated zinc oxide of Example 3 was obtained according to Example 1 except for the fact that the zinc oxide particles (with an average particle diameter of 25 nm; manufactured by Sumitomo Osaka Cement Co., Ltd.) were changed to zinc oxide particles (with an average particle diameter of 35 nm; manufactured by Sumitomo Osaka Cement Co., Ltd.).

Comparative Example 1

The product A produced according to Example 1, which was not subjected to the thermal treatment, was used as a silicon-oxide-coated zinc oxide of Comparative Example 1.

Comparative Example 2

Zinc oxide particles (with an average particle diameter of 35 nm; manufactured by Sumitomo Osaka Cement Co., Ltd.) and water were mixed together and then were ultrasonically dispersed, thereby preparing a zinc oxide aqueous suspension having a content ratio of zinc oxide of 10% by mass.

Next, an aqueous solution of silicate of soda was added to the zinc oxide aqueous suspension so that the content thereof reached 9% by mass in relation to the zinc oxide particles in the zinc oxide aqueous suspension in terms of silicon oxide, and was strongly stirred. The pH of the obtained suspension was 6.5.

Next, 1N hydrochloric acid was added to this suspension, the pH of a liquid mixture was adjusted to 7.0, and the liquid mixture was left to be still for two hours. Then, an oxide of silicon was gradually precipitated on the surfaces of zinc oxide particles, thereby forming a coating.

Next, the suspension was filtered, and the obtained solid substance was washed with water, furthermore, was heated and dried at 105° C. using a dryer, thereby obtaining a silicon-oxide-coated zinc oxide of Comparative Example 2.

Comparative Example 3

A silicon-oxide-coated zinc oxide of Comparative Example 3 was obtained according to Comparative Example 2 except for the fact that the aqueous solution of silicate of soda was added so that the content thereof reached 17% by mass in relation to the zinc oxide particles in the zinc oxide aqueous suspension in terms of silicon oxide.

Comparative Example 4

The silicon-oxide-coated zinc oxide obtained according to Comparative Example 2 was thermally treated at 500° C. for two hours, thereby obtaining a silicon-oxide-coated zinc oxide of Comparative Example 4.

Comparative Example 5

The silicon-oxide-coated zinc oxide obtained according to Comparative Example 3 was thermally treated at 500° C. for two hours, thereby obtaining a silicon-oxide-coated zinc oxide of Comparative Example 5.

Comparative Example 6

A product X was obtained according to Example 1 except for the fact that the amount of the methyl silicate 51 (manufactured by Colcoat Co., Ltd.) was set to reach 25% by mass in relation to zinc oxide particles in terms of silicon oxide.

Next, the product X was heated and dried at 105° C. using a dryer, thereby obtaining a silicon-oxide-coated zinc oxide of Comparative Example 6.

[Evaluation]

The respective silicon-oxide-coated zinc oxides of Examples 1 to 3 and Comparative Examples 1 to 6 were evaluated. The evaluation items are as described below.

(1) Average Particle Diameter

The silicon-oxide-coated zinc oxide was observed using a transmission electron microscope (TEM), 100 particles were selected out, the longest straight line portions (maximum length diameters) of the respective silicon-oxide-coated zinc oxides were measured, and the measurement values were averaged in a weighted manner, thereby computing the average particle diameter.

(2) Infrared Spectroscopy (IR)

The IR evaluation of the silicon-oxide-coated zinc oxide was carried out using a JASCO FT/IR-670 Plus (manufactured by JASCO Corporation) according to the KBr method. Here, a silicon-oxide-coated zinc oxide in which a Si—O—Si expansion and contraction-derived absorption band and a zinc oxide-derived absorption band were respectively observed at 1000 $cm^{-1}$ to 1200 $cm^{-1}$ and 400 $cm^{-1}$ to 600 $cm^{-1}$ was evaluated as "○" and a silicon-oxide-coated zinc oxide in which either or both of the above-described absorption bands were not observed was evaluated as "X".

(3) Degree of Condensation of Silicon Oxide

The NMR spectrum of the silicon-oxide-coated zinc oxide was obtained using solid-state $^{29}Si$ MAS-nuclear magnetic resonance (NMR) spectroscopy and the area ratios $Q^0$, $Q^1$, $Q^2$, $Q^3$, and $Q^4$ of signals attributed to individual environments of $Q^0$, $Q^1$, $Q^2$, $Q^3$, and $Q^4$ were computed from the peak area ratios of the NMR spectrum.

The abundance ratio of silicon in the silicon oxide coating in a $Q^3$ environment was indicated by $Q^3$, the abundance ratio in a $Q^4$ environment was indicated by $Q^4$, and the value of $Q^3+Q^4$ and the value of $Q^4/(Q^3+Q^4)$ were computed. In a case in which $Q^3+Q^4 \geq 0.6$ was satisfied, the silicon-oxide-coated zinc oxide was evaluated as "0", and in a case in which $Q^3+Q^4 \geq 0.6$ was not satisfied, the silicon-oxide-coated zinc oxide was evaluated as "X". In addition, in a case in which $Q^4/(Q^3+Q^4) \geq 0.5$ was satisfied, the silicon-oxide-coated zinc oxide was evaluated as "○", and in a case in which $Q^4/(Q^3+Q^4) \geq 0.5$ was not satisfied, the silicon-oxide-coated zinc oxide was evaluated as "X".

(4) Elution Ratio of Zinc

The silicon-oxide-coated zinc oxide was dispersed in a buffer solution with a pH of 5 so that the content thereof reached 0.05% by mass, the solution was stirred for one hour, then, solids and liquids were separated, and the concentration of liquid-phase zinc was measured using an ICP optical emission spectrometry analyzer.

In addition, the ratio of zinc ions (mol) eluted into the liquid phase to the content (mol) of zinc in the silicon-oxide-coated zinc oxide was considered as the elution ratio of zinc (%).

The buffer solution with a pH of 5 was produced by mixing 500 ml of an aqueous solution of 0.1 M potassium hydrogen phthalate and 226 ml of an aqueous solution of 0.1

M sodium hydroxide and then adding water so that the total amount reached 1000 ml.

These evaluation results are shown in Table 1.

TABLE 1

| | Silicon compound | Thermal treatment (° C.) | SiO$_2$/ZnO (%) | Average particle diameter (nm) | IR | Q$^3$ + Q$^4$ ≥ 0.6 | Q$^4$/(Q$^3$ + Q$^4$) ≥ 0.5 | Elution ratio of zinc (%) |
|---|---|---|---|---|---|---|---|---|
| Example 1 | Methyl silicate 51 | 500 | 10 | 25 | ○ | ○ | ○ | 54 |
| Example 2 | Methyl silicate 51 | 500 | 20 | 25 | ○ | ○ | ○ | 42 |
| Example 3 | Methyl silicate 51 | 500 | 10 | 35 | ○ | ○ | ○ | 57 |
| Comparative Example 1 | Methyl silicate 51 | None | 10 | 25 | ○ | ○ | X | 96 |
| Comparative Example 2 | Silicate of soda | None | 9 | 35 | ○ | X | X | >98 |
| Comparative Example 3 | Silicate of soda | None | 17 | 35 | ○ | ○ | X | 97 |
| Comparative Example 4 | Silicate of soda | 500 | 9 | 35 | ○ | X | X | >98 |
| Comparative Example 5 | Silicate of soda | 500 | 17 | 35 | ○ | ○ | X | 96 |
| Comparative Example 6 | Methyl silicate 51 | None | 25 | 25 | ○ | ○ | X | 96 |

According to Table 1, it was confirmed that, in the silicon-oxide-coated zinc oxides of Examples 1 to 3, compared with the silicon-oxide-coated zinc oxides of Comparative Examples 1 to 6, the values of Q$^3$+Q$^4$ and the values of Q$^4$/(Q$^3$+Q$^4$), which showed the degree of condensation of silicon oxide, were high, and the elution ratios of zinc were low.

Example 4

A silicon-oxide-coated zinc oxide (3 parts by mass) obtained according to Example 2, ascorbic acid (3 parts by mass), and water (94 parts by mass) were mixed together so as to produce a liquid mixture, and the liquid mixture was stirred at room temperature for three hours.

The liquid mixture immediately after the mixing and the liquid mixture after three hours of stirring were both white, and discoloration was barely observed.

Comparative Example 7

The stability on mixing with vitamin C was evaluated in the same manner as in Example 4 except for the fact that a silicon-oxide-coated zinc oxide obtained according to Comparative Example 5 was used instead of the zinc oxide particles (with an average particle diameter of 25 nm; manufactured by Sumitomo Osaka Cement Co., Ltd.) used in Example 2.

The hue of the obtained liquid mixture immediately after the mixing was white; however, as the stirring time elapsed, the liquid mixture became discolored, and, after three hours of stirring, the liquid mixture had discolored to an orange color.

Comparative Example 8

The stability on mixing with vitamin C was evaluated in the same manner as in Example 4 except for the fact that the zinc oxide particles (with an average particle diameter of 25 nm; manufactured by Sumitomo Osaka Cement Co., Ltd.) used in Example 1 were used instead of a silicon-oxide-coated zinc oxide obtained according to Example 2.

The hue of the obtained liquid mixture immediately after the mixing was white; however, as the stirring time elapsed, the liquid mixture became discolored, and, after three hours of stirring, the liquid mixture had discolored to a clear orange color.

From the results of Example 4 and Comparative Examples 7 and 8, it was confirmed that, compared with the silicon-oxide-coated zinc oxides and the zinc oxides of Comparative Examples 7 and 8, the silicon-oxide-coated zinc oxide of Example 4 was coated with a dense silica coating, thus, the decomposition of vitamin C was suppressed, and the stability on mixing with vitamin C was excellent. That is, it was confirmed that the silicon-oxide-coated zinc oxide can be preferably used for organic cosmetic products for which a natural whitening agent or the like is used.

Second Embodiment

Example 5

(1) Silicon-Oxide-Coated Zinc Oxide

Zinc oxide particles (with an average particle diameter of 35 nm; manufactured by Sumitomo Osaka Cement Co., Ltd.) and water were mixed together and then were ultrasonically dispersed, thereby preparing a zinc oxide water-based suspension having a content ratio of zinc oxide of 20% by mass.

Next, this zinc oxide water-based suspension was added to an aqueous solution of silicate of soda that amounted to 5% by mass in relation to the mass of the zinc oxide particles in the zinc oxide water-based suspension in terms of silicon oxide, and was strongly stirred, thereby producing a suspension.

Next, this suspension was heated to 60° C., then, dilute hydrochloric acid was gradually added to the suspension, and the pH was adjusted so as to fall in a range of 6.5 to 7. After that, the suspension was left to be still for two hours and was separated into solids and liquids. The obtained solid substance was washed with water. The solid substance was dried at 150° C., and furthermore, was thermally treated (fired) at 500° C., thereby producing a surface-modified zinc oxide A.

Next, the surface-modified zinc oxide A and methanol were mixed together and then were ultrasonically dispersed, thereby preparing a surface-modified zinc oxide A methanol suspension having a content ratio of the surface-modified zinc oxide A of 10% by mass.

Next, methyl silicate 51 (manufactured by Colcoat Co., Ltd.), methanol, and water were mixed with the surface-modified zinc oxide A methanol suspension so that the total content thereof reached 20% by mass in relation to the zinc oxide in the surface-modified zinc oxide A methanol suspension in terms of silicon oxide. Next, 1 N hydrochloric acid was added to this liquid mixture. The content ratio of the surface-modified zinc oxide A in this liquid mixture was 5% by mass, and the molar ratio between methyl silicate 51, pure water, and hydrochloric acid was 1:10:0.1.

Next, the liquid mixture was heated to 60° C., was held at this temperature for three hours, and was reacted.

After the reaction, solids and liquids were separated through centrifugal separation, and the obtained solid-phase reaction product was dried at 120° C., thereby obtaining a product A.

Next, the product A was thermally treated at 500° C. for two hours, thereby obtaining a silicon-oxide-coated zinc oxide A of Example 5.

Example 6

A surface-modified zinc oxide B of Example 5 was produced according to Example 5 except for the fact that the zinc oxide particles (with an average particle diameter of 35 nm; manufactured by Sumitomo Osaka Cement Co., Ltd.) were changed to zinc oxide particles (with an average particle diameter of 25 nm; manufactured by Sumitomo Osaka Cement Co., Ltd.).

Next, the surface-modified zinc oxide B and 2-propanol were mixed together and then were ultrasonically dispersed, thereby preparing a surface-modified zinc oxide B 2-propanol suspension having a content ratio of the surface-modified zinc oxide B of 10% by mass.

Next, the surface-modified zinc oxide B 2-propanol suspension was heated to 60° C., then, ammonia water and water were added to the suspension under stirring, and the pH was adjusted so as to fall in a range of 10 to 11. Furthermore, a solution of tetramethoxysilane 2-propanol was slowly added dropwise, and was continuously stirred for six hours.

The amount of the tetramethoxysilane added dropwise was 15% by mass in relation to zinc oxide in terms of silicon oxide. In addition, the content of water was 120% by mass of the tetramethoxysilane.

After the reaction, solids and liquids were separated through centrifugal separation, and the obtained solid-phase reaction product was dried at 120° C., thereby obtaining a product B.

Next, the product B was thermally treated at 500° C. for two hours, thereby obtaining a silicon-oxide-coated zinc oxide B of Example 6.

Example 7

A surface-modified zinc oxide C of Example 7 was produced according to Example 6 except for the fact that the content of the aqueous solution of silicate of soda was changed from 5% by mass to 20% by mass in terms of silicon oxide.

Next, a product C and a silicon-oxide-coated zinc oxide C of Example 7 were obtained according to Example 6 using this surface-modified zinc oxide C.

Example 8

A product D and a silicon-oxide-coated zinc oxide D of Example 8 were obtained according to Example 5 except for the fact that, as the surface-modified zinc oxide, SIH20-ZnO350 (with an average particle diameter of 35 nm, $SiO_2/ZnO$=17% by mass; manufactured by Sumitomo Osaka Cement Co., Ltd.) was used instead of the surface-modified zinc oxide A.

Comparative Example 9

The product A produced according to Example 5, which was not subjected to the thermal treatment, was used as a silicon-oxide-coated zinc oxide of Comparative Example 9.

Comparative Example 10

Zinc oxide particles (with an average particle diameter of 25 nm; manufactured by Sumitomo Osaka Cement Co., Ltd.) and water were mixed together and then were ultrasonically dispersed, thereby preparing a zinc oxide water-based suspension having a content ratio of zinc oxide of 10% by mass.

Next, an aqueous solution of silicate of soda was added to the zinc oxide water-based suspension so that the content thereof reached 30% by mass in relation to the zinc oxide particles in the zinc oxide water-based suspension in terms of silicon oxide, and was strongly stirred.

Furthermore, dilute hydrochloric acid was gradually added to the suspension, the addition was stopped when the pH reached 6.5 to 7.0, and the suspension was left to be still for two hours. Then, an oxide of silicon was gradually precipitated on the surfaces of zinc oxide particles, thereby forming a coating. This suspension was filtered, and the obtained solid substance was washed with water, furthermore, was heated and dried at 105° C. for 12 hours using a dryer, thereby obtaining a silicon-oxide-coated zinc oxide of Comparative Example 10.

Comparative Example 11

The silicon-oxide-coated zinc oxide obtained according to Comparative Example 10 was thermally treated at 500° C. for two hours, thereby obtaining a silicon-oxide-coated zinc oxide of Comparative Example 11.

Comparative Example 12

Zinc oxide particles (with an average particle diameter of 25 nm; manufactured by Sumitomo Osaka Cement Co., Ltd.) (200 g) were added to water, and the particles and water were stirred and mixed using a high-speed disperser, thereby preparing a zinc oxide slurry having a content ratio of zinc oxide particles of 10% by mass.

While, the zinc oxide slurry was stirred at room temperature (25° C.), an aqueous solution of silicate of soda that amounted to 20% by mass in terms of silicon oxide (30 g) (3% by mass of silicon oxide in relation to zinc oxide particles) was added thereto. During the addition of the aqueous solution of silicate of soda, hydrochloric acid was added thereto so that the pH of the slurry was maintained in a range of 7 to 8. After that, the slurry was aged for 15 minutes.

The aged slurry was filtered, and the obtained solid substance was washed with water, thereby obtaining a cake-form solid substance (412 g) containing 50% by mass of zinc oxide.

This cake-form solid substance was not dried, 2-propanol (1000 g) was added to the solid substance, and 2-propanol and the solid substance were stirred and mixed together, thereby producing a slurry. Furthermore, deionized water (200 g) and ammonia water (10 g) containing 28% by mass of ammonia were added to the slurry, furthermore, were stirred and mixed together, thereby adjusting the pH in a range of 10 to 11.

While the slurry obtained as described above was stirred using a continuous beads mill UAM-015 (manufactured by Kotobuki Sangyo Co., Ltd.), a liquid mixture obtained by mixing methyl silicate 51 (manufactured by Colcoat Co., Ltd.) (86.3 g) and 2-propanol (42.5 g) was gradually added over six hours.

The obtained slurry was heated and pressurized using a reduced-pressure dryer, thereby distilling water and 2-propanol away. After that, the slurry was further heated up to 150° C. and was held at this temperature for two hours so as to be cured, thereby obtaining a silicon-oxide-coated zinc oxide of Comparative Example 12.

Comparative Example 13

Zinc oxide particles (with an average particle diameter of 25 nm; manufactured by Sumitomo Osaka Cement Co., Ltd.) and methanol were mixed together and then were ultrasonically dispersed, thereby preparing a zinc oxide methanol suspension having a content ratio of zinc oxide of 12.5% by mass.

Next, methyl silicate 51 (manufactured by Colcoat Co., Ltd.), methanol, and water were mixed with the zinc oxide methanol suspension so that the total content thereof reached 20% by mass in relation to the zinc oxide particles in the zinc oxide methanol suspension in terms of silicon oxide. Next, 1 N hydrochloric acid was added to this liquid mixture, then, the liquid mixture was heated to 60° C., was held at this temperature for three hours, and was reacted.

The content ratio of zinc oxide in this reaction liquid was 5% by mass, and the molar ratio between methyl silicate 51, pure water, and hydrochloric acid was 1:10:0.1.

After the reaction, solids and liquids were separated through centrifugal separation, and the obtained solid-phase reaction product was dried at 120° C., thereby obtaining a product.

Next, the solid-phase dried substance was thermally treated (fired) at 500° C. for two hours, thereby obtaining a silicon-oxide-coated zinc oxide of Comparative Example 13.

[Evaluation]

The respective silicon-oxide-coated zinc oxides of Examples 5 to 8 and Comparative Examples 9 to 13 were evaluated. The evaluation items are as described below.

(1) Average Particle Diameter

The silicon-oxide-coated zinc oxide was observed using a transmission electron microscope (TEM), 200 particles were selected out, the longest straight line portions (maximum length diameters) of the respective silicon-oxide-coated zinc oxides were measured, and the measurement values were averaged in a weighted manner, thereby computing the average particle diameter.

As an example of a transmission electron microscopic (TEM) image of the silicon-oxide-coated zinc oxide, FIG. 1 illustrates a transmission electron microscopic (TEM) image of the silicon-oxide-coated zinc oxide of Example 7.

(2) Infrared Spectroscopy (IR)

The IR evaluation of the silicon-oxide-coated zinc oxide was carried out using a JASCO FT/IR-670 Plus (manufactured by JASCO Corporation) according to the KBr method. Here, a silicon-oxide-coated zinc oxide in which a Si—O—Si expansion and contraction-derived absorption band and a zinc oxide-derived absorption band were respectively observed at 1000 $cm^{-1}$ to 1200 $cm^{-1}$ and 400 $cm^{-1}$ to 600 $cm^{-1}$ was evaluated as "0" and a silicon-oxide-coated zinc oxide in which either or both of the above-described absorption bands were not observed was evaluated as "X".

(3) Degree of Condensation of Silicon Oxide

The NMR spectrum of the silicon-oxide-coated zinc oxide was obtained using solid-state $^{29}Si$ MAS-nuclear magnetic resonance (NMR) spectroscopy and the area ratios $Q^0$, $Q^1$, $Q^2$, $Q^3$, and $Q^4$ of signals attributed to individual environments of $Q^0$, $Q^1$, $Q^2$, $Q^3$, and $Q^4$ were computed from the peak area ratios of the NMR spectrum.

The value of $Q^3+Q^4$ and the value of $Q^4/(Q^3+Q^4)$ when the abundance ratio of silicon in the silicon oxide coating in a $Q^3$ environment was indicated by $Q^3$ and the abundance ratio in a $Q^4$ environment was indicated by $Q^4$ were computed.

Figure 2:
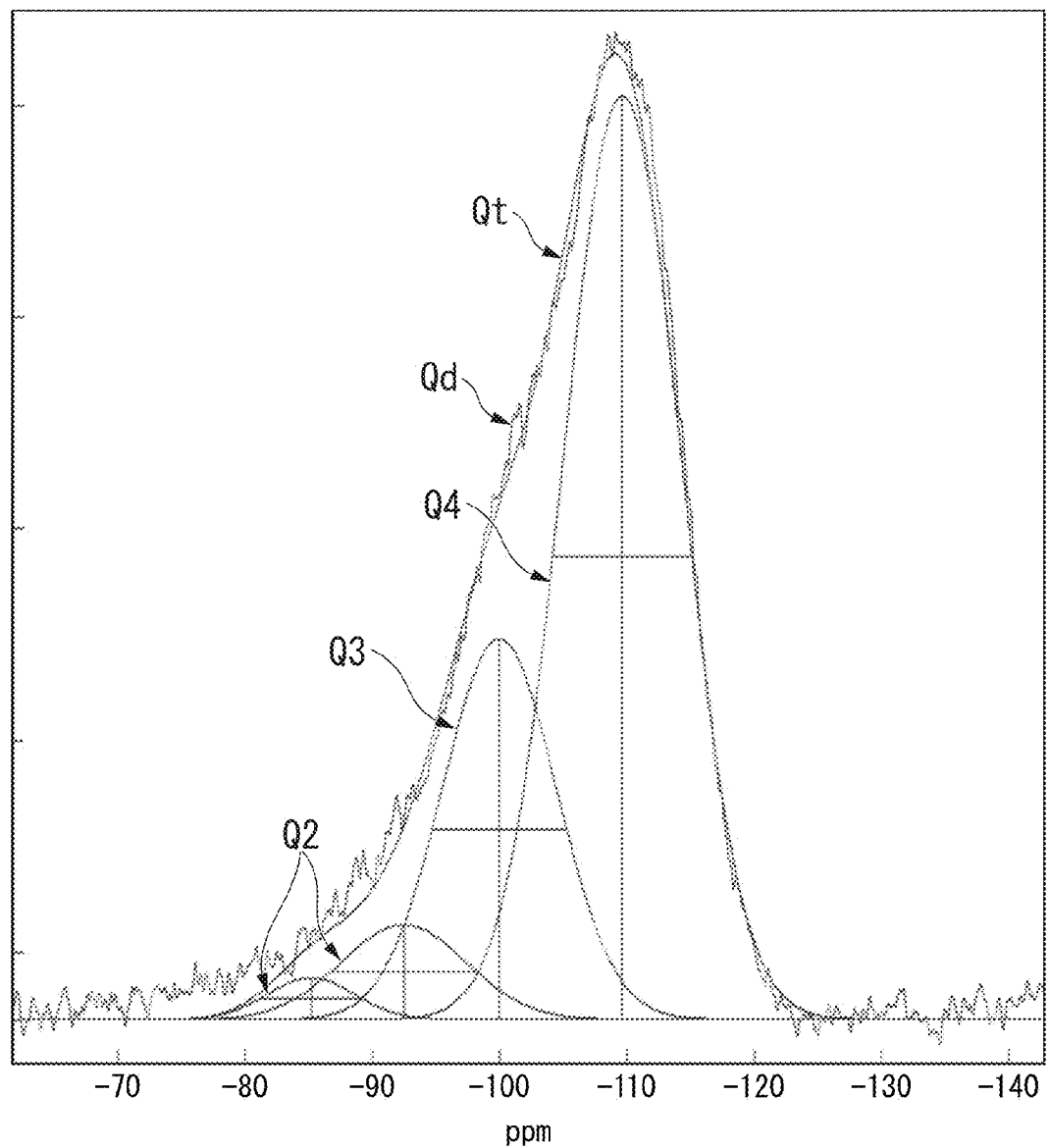
FIG. 2 is a diagram illustrating an NMR spectrum of the silicon-oxide-coated zinc oxide of Example 7 of the present invention.
Figure 3:
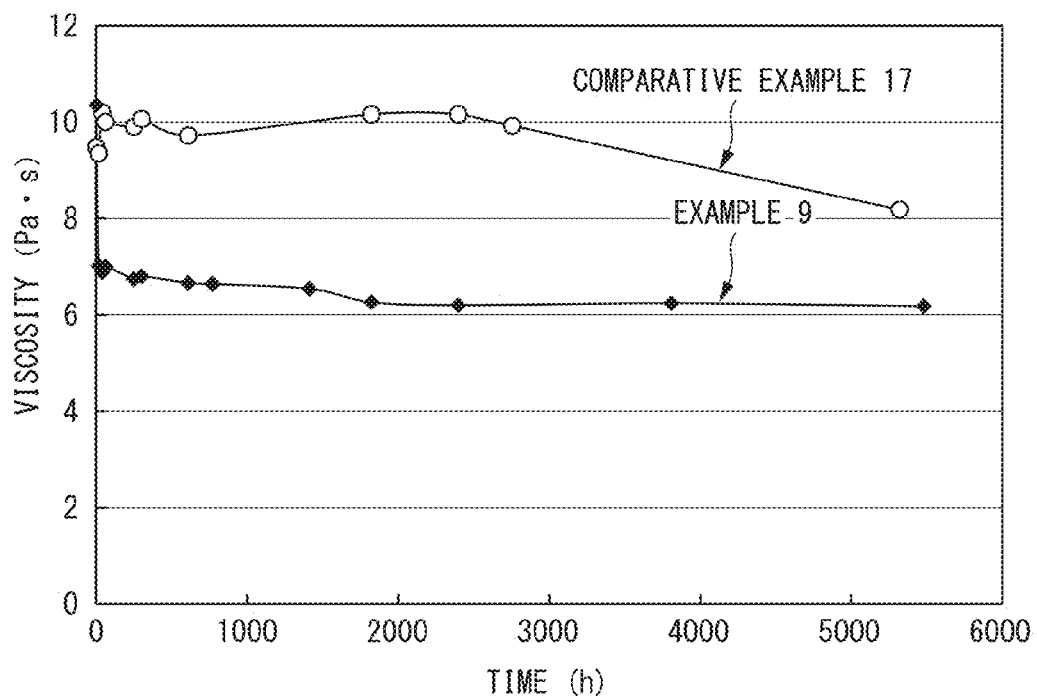
FIG. 3 is a diagram illustrating changes in viscosity over time at 40° C. of a silicon-oxide-coated-zinc-oxide-containing composition of Example 9 of the present invention and an aqueous solution of a carbomer of Comparative Example 17.

As an example of the NMR spectrum, FIG. 2 illustrates an NMR spectrum of the silicon-oxide-coated zinc oxide of Example 7.

In FIG. 2, in order to prevent superscripts from becoming unclear, the actual NMR spectrum measurement data Qd is indicated by "Qd", $Q^2$, $Q^3$, and $Q^4$ on which waveform separation was carried out so as to fit the measurement data Qd are indicated by "Q2", "Q3", and "Q4", and the NMR spectrum Qt obtained by summing the waveform-separated NMR spectra $Q^2$, $Q^3$, and $Q^4$ is indicated by "Qt".

According to FIG. 2, the NMR spectrum Qt matched the actual measurement data Qd well.

(4) Elution Ratio of Zinc

The silicon-oxide-coated zinc oxide was dispersed in a buffer solution with a pH of 5 so that the content thereof reached 0.05% by mass, the solution was stirred for one hour, then, solids and liquids were separated, and the concentration of liquid-phase zinc was measured using an ICP optical emission spectrometry analyzer.

In addition, the ratio of zinc ions (mol) eluted into the liquid phase to the content (mol) of zinc in the silicon-oxide-coated zinc oxide was considered as the elution ratio of zinc (%).

The buffer solution with a pH of 5 was produced by mixing 500 ml of an aqueous solution of 0.1 M potassium hydrogen phthalate and 226 ml of an aqueous solution of 0.1 M sodium hydroxide and then adding water so that the total amount reached 1000 ml.

(5) Decomposition Ratio of Brilliant Blue

An aqueous solution of Brilliant Blue having a content ratio of Brilliant Blue adjusted to 5 ppm was produced, and the silicon-oxide-coated zinc oxide that amounted to 0.15 g in terms of zinc oxide was injected into 15 g of this aqueous solution of Brilliant Blue and was ultrasonically dispersed so as to prepare a suspension. This suspension was irradiated using an ultraviolet lamp (with a central wavelength of 254 nm) at an irradiation distance of 10 cm for six hours, and then, the supernatant solution was sampled.

Next, the respective absorptiometric spectra of the aqueous solution of Brilliant Blue and the supernatant solution were obtained using atomic absorption spectrometry, and the decomposition ratio D of Brilliant Blue was computed using these measurement values from Expression (1) described above.

The material compositions and the like and the evaluation results of the respective silicon-oxide-coated zinc oxides of Examples 5 to 8 and Comparative Examples 9 to 13 are shown in Tables 2 and 3.

In addition, the measurement results of the elution ratio of zinc and the decomposition ratio of Brilliant Blue of zinc oxide particles (with an average particle diameter of 25 nm; manufactured by Sumitomo Osaka Cement Co., Ltd.) used in Example 6 are shown in Tables 2 and 3 as Comparative Example 14.

According to Tables 2 and 3, it was confirmed that, in the silicon-oxide-coated zinc oxides of Examples 5 to 8, compared with the silicon-oxide-coated zinc oxides of Comparative Examples 9 to 13, the values of $Q^3+Q^4$ and the values of $Q^4/(Q^3+Q^4)$ which showed the degree of condensation of silicon oxide, were high, the elution ratios of zinc and the decomposition ratios of Brilliant Blue were low, and dense and uniform silicon oxide coatings were formed on the surfaces of the zinc oxide particles.

TABLE 2

| | Surface modification | | Silicon oxide coat | | Thermal treatment (° C.) | Average particle diameter (nm) | IR |
|---|---|---|---|---|---|---|---|
| | Raw material | % by mass | Raw material | % by mass | | | |
| Example 5 | Silicate of soda | 5 | methyl silicate 51 | 20 | ○ | 35 | ○ |
| Example 6 | Silicate of soda | 5 | TMOS | 15 | ○ | 25 | ○ |
| Example 7 | Silicate of soda | 20 | TMOS | 15 | ○ | 25 | ○ |
| Example 8 | Silicate of soda | 17 | TMOS | 15 | ○ | 35 | ○ |
| Comparative Example 9 | Silicate of soda | 5 | methyl silicate 51 | 20 | — | 35 | ○ |
| Comparative Example 10 | Silicate of soda | 30 | — | — | — | 25 | ○ |
| Comparative Example 11 | Silicate of soda | 30 | — | — | ○ | 25 | ○ |
| Comparative Example 12 | Silicate of soda | 3 | methyl silicate 51 | 22 | — | 25 | ○ |
| Comparative Example 13 | — | — | methyl silicate 51 | 20 | ○ | 25 | ○ |
| Comparative Example 14 | — | — | — | — | — | 25 | — |

(NOTE)
TMOS: Tetramethoxysilane

TABLE 3

| | $Q^3 + Q^4$ | $Q^4/(Q^3 + Q^4)$ | Elution ratio of zinc (%) | Decomposition ratio of Brilliant Blue (%) |
|---|---|---|---|---|
| Example 5 | 0.61 | 0.50 | 17 | <1.0 |
| Example 6 | 0.82 | 0.78 | 19 | 1.7 |
| Example 7 | 0.92 | 0.76 | 5 | <1.0 |
| Example 8 | 0.91 | 0.71 | 14 | <1.0 |
| Comparative Example 9 | 0.67 | 0.22 | 88 | <1.0 |
| Comparative Example 10 | 0.74 | 0.26 | >98 | <1.0 |
| Comparative Example 11 | 0.74 | 0.36 | >98 | <1.0 |
| Comparative Example 12 | 0.76 | 0.46 | 96 | 8.2 |
| Comparative Example 13 | 0.95 | 0.81 | 42 | 7.4 |
| Comparative Example 14 | — | — | >98 | 90 |

(2) Silicon-Oxide-Coated-Zinc-Oxide-Containing Composition

Example 9

A carbomer Ultrez 10 (manufactured by Nikko Chemicals Co., Ltd.) (1.5 g) was dissolved in pure water, and then an aqueous solution of 10% by mass of sodium hydroxide was added dropwise so as to adjust the pH, thereby producing an aqueous solution of a carbomer containing 1.5% by mass of the carbomer and having a pH of 7.5.

Next, this aqueous solution of a carbomer and a silicon-oxide-coated zinc oxide C obtained in the same manner as in Example 7 were mixed together at a mass ratio of 95:5, thereby obtaining a silicon-oxide-coated-zinc-oxide-containing composition of Example 9.

The viscosity of the composition was measured using a BII-type viscometer (manufactured by Toki Sangyo Co., Ltd.) under conditions of 20° C. and 30 rpm and was found to be 10.4 Pa·s.

A predetermined amount of this composition was sampled, and this sampled specimen was held at 40° C. using a constant-temperature bath, and the viscosity was measured every predetermined time under conditions of 20° C. and 30 rpm. The results for the viscosity are shown in Table 3.

Comparative Example 15

A zinc-oxide-containing composition of Comparative Example 15 was obtained in the same manner as in Example 9 except for the fact that the zinc oxide particles (with an average particle diameter of 35 nm; manufactured by Sumitomo Osaka Cement Co., Ltd.) were used instead of a silicon-oxide-coated zinc oxide C obtained in the same manner as in Example 7.

The viscosity of the composition was measured in the same manner as in Example 9 and was found to be 2.4 Pa·s.

Comparative Example 16

Water (5700 g) was added to zinc oxide particles (with an average particle diameter of 25 nm; manufactured by Sumitomo Osaka Cement Co., Ltd.) (300 g), and water and the particles were stirred and mixed using a high-speed disperser, thereby preparing a zinc oxide slurry having a content ratio of zinc oxide particles of 5% by mass.

This zinc oxide slurry was heated to 80° C. under stirring, and then an aqueous solution of silicate of soda that amounted to 20% by mass in terms of silicon oxide (7.5 g) (10% by mass of silicon oxide in relation to zinc oxide particles) was added thereto. During the addition of the aqueous solution of silicate of soda, hydrochloric acid was appropriately added thereto so that the pH of the slurry was maintained in a range of 6 to 7. After that, the slurry was aged for 15 minutes.

Next, an aqueous solution of sodium aluminate that amounted to 5% by mass in relation to the total mass of zinc oxide particles in terms of aluminum oxide ($Al_2O_3$) (10% by mass of the aqueous solution of sodium aluminate) was added to the slurry under stirring, the slurry was aged for 10 minutes, and then hydrochloric acid was added so that the pH of the slurry was adjusted to 7.

After that, the slurry was aged for 30 minutes, and the obtained suspension was filtered, washed with water, and dried at 130° C. for 12 hours, and then the suspension was crushed using a jet mill, thereby obtaining surface-coated zinc oxide particles of Comparative Example 16 in which the surfaces of the zinc oxide particles were coated with silicon oxide and aluminum oxide.

The elution ratio of zinc of the surface-coated zinc oxide particles was measured in the same manner as in Example 5 and was found to be 97%.

Next, a surface-coated zinc-oxide-containing composition of Comparative Example 16 was obtained in the same manner as in Example 9 except for the fact that the above-described surface-coated zinc oxide particles were used instead of a silicon-oxide-coated zinc oxide obtained in the same manner as in Example 7.

The viscosity of the composition was measured in the same manner as in Example 9 and was found to be 2.5 Pa·s.

Comparative Example 17

A carbomer Ultrez 10 (manufactured by Nikko Chemicals Co., Ltd.) (1.5 g) was dissolved in pure water, and then an aqueous solution of 10% by mass of sodium hydroxide was added dropwise so as to adjust the pH, thereby producing an aqueous solution of a carbomer containing 1.5% by mass of the carbomer and having a pH of 7.5.

Next, this aqueous solution of a carbomer and pure water were mixed together at a mass ratio of 95:5, and then were stirred, thereby obtaining an aqueous solution of a carbomer of Comparative Example 17.

Next, the viscosity of the aqueous solution of a carbomer was measured in the same manner as in Example 9 and was found to be 9.5 Pa·s.

A predetermined amount of this aqueous solution of a carbomer was sampled, and this sampled specimen was held at 40° C. using a constant-temperature bath, and the viscosity was measured every predetermined time under conditions of 20° C. and 30 rpm. The results for the viscosity are shown in Table 3.

According to the above-described results, it was confirmed that, in the silicon-oxide-coated-zinc-oxide-containing composition of Example 9, the elution ratio of zinc was sufficiently suppressed, and, while the viscosity decreased for approximately up to 15 hours from the production of the composition, the viscosity remained constant thereafter, and the decrease in the viscosity was suppressed.

In addition, it was confirmed that, due to a change over time, the viscosity decreased to a small extent in the beginning; however, when a certain period of time elapsed, the following decrease in the viscosity was suppressed.

Meanwhile, it was confirmed that, in the composition of Comparative Example 15, the elution ratio of zinc of the blended zinc oxide was high, and furthermore, the viscosity decreased immediately after the production of the composition.

In the composition of Comparative Example 16, it was confirmed that the zinc ion elution-suppressing effect of the zinc oxide particles coated with silicon oxide and aluminum oxide was not sufficient, and thus the elution ratio of zinc became high, and furthermore, phases were separated immediately after the production of the composition, and the viscosity was decreased.

In Comparative Example 17, since the aqueous solution of a carbomer did not include zinc oxide, there was no influence of the holding time at 40° C., and the viscosity was constant at approximately 10 Pa·s.

Example 10

A silicon-oxide-coated zinc oxide C (30 parts by mass) obtained in the same manner as in Example 7, hydrogen dimethicone KF-9901 (manufactured by Shin-Etsu Chemical Co., Ltd.) (1.2 parts by mass), and isopropyl alcohol (68.8 parts by mass) were mixed together and were stirred at 60° C. for three hours.

Next, the solvent was removed, and the mixture was thermally treated at 150° C. for 15 hours, thereby obtaining a silicon-oxide-coated zinc oxide E surface-treated with the silicone of Example 10.

Example 11

A silicon-oxide-coated zinc oxide E (30 parts by mass) surface-treated with the silicone obtained in the same manner as in Example 10, polyether-modified silicone SH3775M (manufactured by Dow Corning Toray Co., Ltd.) (4.5 parts by mass), and decamethylcyclopentasiloxane (D5) (65.5 parts by mass) were mixed together, and then were dispersed using a beads mill, thereby obtaining a silicon-oxide-coated-zinc-oxide-containing composition of Example 11.

The dispersed particle diameter of the silicon-oxide-coated zinc oxide E in this composition was measured using a particle size analyzer LB-550 (manufactured by Horiba, Ltd.), and the average dispersed particle diameter (D50) was 156 nm.

A composition obtained by diluting the above-described composition with decamethylcyclopentasiloxane (D5) so that the content of the silicon-oxide-coated zinc oxide reached 15% by mass was applied onto a silica substrate using a bar coater, thereby forming a 32 μm-thick coating.

The light transmission of this coating was obtained using a SPF analyzer UV-1000S (manufactured by Labsphere, Inc.), and was found to be 57% at 450 nm.

Evaluation of Stability on Mixing with Vitamin C

For each of the silicon-oxide-coated zinc oxides obtained according to Example 7 and Comparative Example 11 and the zinc oxide used in Comparative Example 14, the stability on mixing with vitamin C was evaluated.

Example 12

A silicon-oxide-coated zinc oxide (3 parts by mass) of Example 7, ascorbic acid (3 parts by mass), and water (94 parts by mass) were mixed together so as to produce a liquid mixture, and the liquid mixture was stirred at room temperature for three hours.

The liquid mixture immediately after the mixing and the liquid mixture after three hours of stirring were both white, and discoloration was barely observed.

In addition, the liquid mixture after three hours of stirring was centrifugally separated, the supernatant solution was collected, and the chromaticity of the supernatant solution was measured using a spectroscopic color difference meter Color Meter SE-2000 (manufactured by Nippon Denshoku Industries Co., Ltd.). As a result, it was found that the supernatant solution had an L* value of 99.08, an a* value of −0.23, and a b* value of 1.99.

Comparative Example 18

The stability on mixing with vitamin C was evaluated in the same manner as in Example 12 except for the fact that the silicon-oxide-coated zinc oxide of Comparative Example 11 was used instead of the silicon-oxide-coated zinc oxide of Example 7.

The hue of the obtained liquid mixture immediately after the mixing was white; however, as the stirring time elapsed, the liquid mixture became discolored, and, after three hours of stirring, the liquid mixture had discolored to an orange color.

As a result of measuring the chromaticity of the supernatant solution in the same manner as in Example 12, it was found that the L* value was 97.88, the a* value was −1.26, and the b* value was 3.02, the value of the b* value indicating yellow color was higher than Example 12, and the degree of discoloration was large.

Comparative Example 19

The stability on mixing with vitamin C was evaluated in the same manner as in Example 12 except for the fact that the zinc oxide used in Comparative Example 14 was used instead of the silicon-oxide-coated zinc oxide of Example 7.

The hue of the obtained liquid mixture immediately after the mixing was white; however, as the stirring time elapsed, the liquid mixture became discolored, and, after three hours of stirring, the liquid mixture had discolored to a clear orange color.

As a result of measuring the chromaticity of the supernatant solution in the same manner as in Example 12, it was found that the L* value was 98.03, the a* value was −2.69, and the b* value was 8.25, the value of the b* value indicating yellow color was extremely higher than Example 12, and the degree of discoloration was extremely large.

From the results of Example 12 and Comparative Examples 18 and 19, it was confirmed that, compared with the silicon-oxide-coated zinc oxide of Comparative Example 18 and the silicon-oxide-coated zinc oxide of Comparative Example 19, the silicon-oxide-coated zinc oxide of Example 12 was coated with a dense and uniform silica coating, thus, the decomposition of vitamin C was suppressed, and the stability on mixing with vitamin C was excellent. That is, it was confirmed that the silicon-oxide-coated zinc oxide can be preferably used for organic cosmetic products for which a natural whitening agent or the like is used.

INDUSTRIAL APPLICABILITY

In the silicon-oxide-coated zinc oxide of the present invention, since the average particle diameter of the zinc oxide particles in the silicon-oxide-coated zinc oxide formed by coating the surfaces of zinc oxide particles with a silicon oxide coating is set in a range of 1 nm or more and 50 nm or less, and, when the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied, it is possible to suppress the elution of zinc ions from the zinc oxide particles to the outside, and, in a case in which the silicon-oxide-coated zinc oxide is applied to a cosmetic, it is possible to suppress the degradation of performance as a cosmetic, discoloration, a change in the viscosity, and the like which are caused by the elution of zinc ions. As a result, the silicon-oxide-coated zinc oxide can be reliably applied to cosmetic products which require ultraviolet ray-screening performance and have excellent feeling during use, and, even in a case in which the silicon-oxide-coated zinc oxide is used in fields other than cosmetic products, there is a wide range of choice for dispersants or resins, and it is possible to increase the degree of freedom in design and formulation of paints and the like. Therefore, the silicon-oxide-coated zinc oxide has a large industrial value.

In addition, in the silicon-oxide-coated zinc oxide of the present invention, since the average particle diameter of the zinc oxide particles in the silicon-oxide-coated zinc oxide formed by coating the surfaces of zinc oxide particles with a dense silicon oxide coating is set in a range of 1 nm or more and 50 nm or less, when the abundance ratio of silicon in the silicon oxide coating in a $Q^3$ environment is indicated by $Q^3$, and the abundance ratio in a $Q^4$ environment is indicated by $Q^4$, $Q^3+Q^4 \geq 0.6$ and $Q^4/(Q^3+Q^4) \geq 0.5$ are satisfied, and the decomposition ratio of Brilliant Blue generated by the photocatalytic activity of the zinc oxide particles is set to 3% or less, it is possible to suppress the elution of zinc ions from the zinc oxide particles to the outside, and, in a case in which the silicon-oxide-coated zinc oxide is applied to a cosmetic, it is possible to suppress the degradation of performance as a cosmetic, discoloration, a change in the viscosity, and the like which are caused by the elution of zinc ions. As a result, the silicon-oxide-coated zinc oxide can be reliably applied to cosmetic products which require ultraviolet ray-screening performance and have excellent feeling during use, and, even in a case in which the silicon-oxide-coated zinc oxide is used in fields other than cosmetic products, there is a wide range of choice for dispersants or resins, and it is possible to increase the degree of freedom in design and formulation of paints and the like. Therefore, the silicon-oxide-coated zinc oxide has a large industrial value.

The invention claimed is:

1. A silicon-oxide-coated zinc oxide formed by coating the surfaces of zinc oxide particles with a silicon oxide coating, wherein the average particle diameter of the zinc oxide particles is in a range of 1 nm to 50 nm, and when the abundance ratio of silicon in the silicon oxide coating in a $Q^3$ environment is indicated by $Q^3$, and the abundance ratio in a $Q^4$ environment is indicated by $Q^4$, $Q^3+Q^4>0.6$ and $Q^4/(Q^3+Q^4)>0.5$.

2. The silicon-oxide-coated zinc oxide according to claim 1, wherein the content ratio of the zinc oxide particles is in a range of 50% by mass to 90% by mass.

3. The silicon-oxide-coated zinc oxide according to claim 1, wherein, when the silicon-oxide-coated zinc oxide is immersed in an aqueous solution having a pH of 5 so that the content thereof reaches 0.05% by mass, the elution ratio of zinc being eluted in the aqueous solution is 60% by mass or less.

4. The silicon-oxide-coated zinc oxide according to claim 1, wherein the decomposition ratio of Brilliant Blue generated by the photocatalytic activity of the zinc oxide particles is 3% or less.

5. The silicon-oxide-coated zinc oxide according to claim 4, wherein the content ratio of the zinc oxide particles is in a range of 50% by mass to 90% by mass.

6. The silicon-oxide-coated zinc oxide according to claim 4, wherein, when the silicon-oxide-coated zinc oxide is immersed in an aqueous solution having a pH of 5 so that the content thereof reaches 0.05% by mass, the elution ratio of zinc being eluted in the aqueous solution is 20% by mass or less.

7. The silicon-oxide-coated zinc oxide according to claim 1, wherein the surfaces of the silicon-oxide-coated zinc oxide are surface-treated with a silicone resin.

8. A method for manufacturing the silicon-oxide-coated zinc oxide according to claim 1, wherein zinc oxide particles are suspended in a solvent so as to produce a zinc oxide suspension, next, any one or more of alkoxysilanes and oligomers of an alkoxysilane which are decamers or lower oligomers, a catalyst, and water are added to and reacted with the zinc oxide suspension, and then the obtained reaction product is thermally treated at a temperature in a range of 200° C. to 550° C.

9. A method for manufacturing the silicon-oxide-coated zinc oxide according to claim 4, wherein a surface-modified zinc oxide is suspended in a solvent so as to produce a surface-modified zinc oxide suspension, next, any one or more of alkoxysilanes and oligomers of an alkoxysilane which are decamers or lower oligomers, a catalyst, and water are added to and reacted with the surface-modified zinc oxide suspension, and then the obtained reaction product is thermally treated at a temperature in a range of 200° C. to lower than 600° C.

10. A silicon-oxide-coated-zinc-oxide-containing composition comprising:

the silicon-oxide-coated zinc oxide according to claim 1 and a solvent.

11. The silicon-oxide-coated-zinc-oxide-containing composition according to claim 10, further comprising:

a viscosity improver.

12. A cosmetic formed by including the silicon-oxide-coated zinc oxide according to claim 1 in a cosmetic base.

13. A cosmetic formed by including the silicon-oxide-coated-zinc-oxide-containing composition according to claim 10 in a cosmetic base.

* * * * *